United States Patent
Hill et al.

(10) Patent No.: US 9,879,044 B2
(45) Date of Patent: Jan. 30, 2018

(54) METHODS, COMPOSITIONS, AND KITS USING HETEROGENEOUS CATALYSTS

(71) Applicant: OCCIDENTAL COLLEGE, Los Angeles, CA (US)

(72) Inventors: Michael Hill, Pasadena, CA (US); Andrew Udit, Glendale, CA (US)

(73) Assignee: OCCIDENTAL COLLEGE, Los Angeles, CA (US)

( * ) Notice: Subject to any disclaimer, the term of this patent is extended or adjusted under 35 U.S.C. 154(b) by 0 days.

(21) Appl. No.: 15/168,911

(22) Filed: May 31, 2016

(65) Prior Publication Data
US 2016/0347785 A1 Dec. 1, 2016

Related U.S. Application Data

(60) Provisional application No. 62/169,350, filed on Jun. 1, 2015.

(51) Int. Cl.
*C07H 21/04* (2006.01)
*B01J 31/08* (2006.01)
*B01J 35/04* (2006.01)
*B01J 31/18* (2006.01)
*B01J 37/16* (2006.01)
*B01J 23/72* (2006.01)

(52) U.S. Cl.
CPC .............. *C07H 21/04* (2013.01); *B01J 23/72* (2013.01); *B01J 31/08* (2013.01); *B01J 31/183* (2013.01); *B01J 37/16* (2013.01)

(58) Field of Classification Search
CPC ......... C07H 21/04; B01J 31/183; B01J 31/08; B01J 35/04
See application file for complete search history.

(56) References Cited

U.S. PATENT DOCUMENTS

| | | |
|---|---|---|
| 7,375,234 B2 | 5/2008 | Sharpless et al. |
| 2012/0035335 A1 | 2/2012 | Ladet et al. |
| 2012/0100633 A1 | 4/2012 | Manetto et al. |

FOREIGN PATENT DOCUMENTS

| | | |
|---|---|---|
| CN | 103920308 A | 7/2014 |
| WO | WO-2016196492 A1 | 12/2016 |

OTHER PUBLICATIONS

Pereira et al. Flow injection spectrophotometric determination of L-ascorbic acid in pharmaceutical formulations with on-line solid-phase reactor containing copper (II) phosphate. Analytica Chimica Acta 366:55-62, 1998.*
Harris, Sarah, "Heterogeneous Click reactions for biological conjugations" (2009). URC Student Scholarship. http://scholar.oxy.edu/urc_student/849.*
Harris, Sarah, "A New Heterogeneous Method of Click Reactions for Biological Conjugations" (2010). URC Student Scholarship. http://scholar.oxy.edu/urc_student/851.*
Presolski et al. Resin-Supported Catalysts for CuAAC Click Reactions in Aqueous or Organic Solvents. ACS Comb. Sci. 14:527-530, 2012.*
Collinson et al. Reusable and highly active supported copper(I)—NHC catalysts for Click chemistry. Chem Commun 49:11358-11360 (2013).
Gholinejad et al. Copper Nanoparticles Supported on Agarose as a Bioorganic and Degradable Polymer for Multicomponent Click Synthesis of 1,2,3-Triazoles under Low Copper Loading in Water. ACS Sustainable Chem Eng 2(12):2658-2665 (2014).
Hashemi et al. In situ prepared CuI nanoparticles on modified poly(styrene-co-maleic anhydride): an efficient and recyclable catalyst for the azide-alkyne click reaction in water. Transition Met Chem 39:593-601 (2014).
Hong et al. Analysis and optimization of copper-catalyzed azide-alkyne cycloaddition for bioconjugation. Angew Chem Int Ed 48:9879-9883 (2009).
Hong et al. Electrochemically protected copper(I)—catalyzed azide-alkyne cycloaddition. ChemBioChem 9:1481-1486 (2008).
Kallick et al. Heterogeneous catalysis for azide-alkyne bioconjugation in solution via spin column: Attachment of dyes and saccharides to peptides and DNA. BioTechniques 59:329-334 (2015).
Kumar et al. Aminoclay-supported copper nanoparticles for 1,3-dipolar cycloaddition of azides with alkynes via click chemistry. J Nanosci Nanotechnol 13(4):3136-3141 (2013).
Nasrollahzadeh et al. Synthesis and catalytic activity of carbon supported copper nanoparticles for the synthesis of aryl nitriles and 1,2,3-triazoles. RSC Adv. 5:2785-2793 (2015).
Pourjavadi et al. Magnetic nanoparticles entrapped in the cross-linked poly(imidazole/imidazolium) immobilized Cu(II): an effective heterogeneous copper catalyst. RSC Adv. 4:46418-46426 (2014).
Sun et al. Recyclable porous polymer-supported copper catalysts for Glaser and Huisgen 1,3-diolar cycloaddition reactions. Chem Asian J 8(11):2822-2827 (2013).
Xiong et al. Supported CuBr on graphene oxide/Fe3O4: a highly efficient, magnetically separable catalyst for the multi-gram scale synthesis of 1,2,3-triazoles. RSC Adv 4:9830-9837 (2014).
Hewat et al. Neutral copper(I) dipyrrin complexes and their use as sensitizers in dye-sensitized solar cells. Dalton Trans 43(10):4127-4136 (2014).
PCT/US2016/035063 International Search Report and Written Opinion dated Sep. 19, 2016.

* cited by examiner

*Primary Examiner* — Yih-Horng Shiao
(74) *Attorney, Agent, or Firm* — Wilson Sonsini Goodrich & Rosati

(57) ABSTRACT

Described herein are methods, compositions and kits utilizing heterogeneous metal catalysts for the preparation of cycloaddition compounds, such as triazoles and biomolecules.

24 Claims, 5 Drawing Sheets

SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Arg Arg Arg Arg Arg Arg Arg
1               5

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' ethynyl-(CH2)6

<400> SEQUENCE: 2
gctcagtacg acgtcga                                                    17

METHODS, COMPOSITIONS, AND KITS USING HETEROGENEOUS CATALYSTS

CROSS-REFERENCE

This application claims the benefit of U.S. Provisional Patent Application No. 62/169,350, filed on Jun. 1, 2015, which is incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jul. 14, 2016, is named 48121-701 201 SL.txt and is 781 bytes in size.

STATEMENT AS TO FEDERALLY SPONSORED RESEARCH

This invention was made with government support under Contract Number 1402029 by the National Science Foundation. The government has certain rights in the invention.

BACKGROUND OF THE INVENTION

Transition metal-catalyzed azide-alkyne cycloaddition is widely used in the chemical modification of molecules and has demonstrated utility, particularly for bio-orthogonal conjugation reactions.

SUMMARY OF THE INVENTION

Described herein are methods, compositions, and kits for the preparation of cycloaddition compounds (e.g., triazole compounds from the azide-alkyne cycloaddition), including biomolecules, using a heterogeneous metal catalyst. The methods provided herein provide a convenient syntheses and purification procedure using heterogeneous metal catalysts.

In one aspect, provided herein is a method for preparing a cycloaddition compound from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (I) catalyst; and passing the solution containing the alkyne component and the azide component through the column; wherein upon contact with the copper (I) catalyst within the matrix, the alkyne component and the azide component react to form the cycloaddition compound.

In another aspect, provided herein is a method for preparing a cycloaddition compound from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (II) precatalyst and a reducing agent; wherein a copper (I) catalyst is generated from the reduction of the copper (II) precatalyst with the reducing agent; and passing the solution containing the alkyne component and the azide component through the column; wherein upon contact with the copper (I) catalyst within the matrix, the alkyne component and the azide component react to form the cycloaddition compound.

In another aspect, provided herein is a method for preparing a cycloaddition compound from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the column; wherein upon contact with the copper (I) catalyst within the matrix, the alkyne component and the azide component react to form the cycloaddition compound.

In some embodiments, the column is suitable use in gravity column chromatography or centrifugal column chromatography. In some embodiments, passing the solution containing the alkyne component and the azide component through the column is through gravity. In certain embodiments, passing the solution containing the alkyne component and the azide component through the column further comprises the use of positive pressure from air or a compressed gas. In some embodiments, passing the solution containing the alkyne component and the azide component through the column is through centrifuging the column for a sufficient period of time.

In another aspect, provided herein is a method for preparing a cycloaddition compound from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (I) catalyst; and passing the solution containing the alkyne component and the azide component through the centrifuge column by centrifuging the centrifuge column for a sufficient period of time; wherein upon contact with the copper (I) catalyst within the matrix, the alkyne component and the azide component react to form the cycloaddition compound.

In another aspect, provided herein is a method for preparing a cycloaddition compound from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (II) precatalyst and a reducing agent; wherein a copper (I) catalyst is generated from the reduction of the copper (II) precatalyst with the reducing agent; and passing the solution containing the alkyne component and the azide component through centrifuge column by centrifuging the centrifuge column for a sufficient period of time; wherein upon contact with the copper (I) catalyst within the matrix, the alkyne component and the azide component react to form the cycloaddition compound.

In another aspect, provided herein is a method for preparing a cycloaddition compound from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the centrifuge column by centrifuging the centrifuge column for a sufficient period of time; wherein upon contact with the copper (I) catalyst within the matrix, the alkyne component and the azide component react to form the cycloaddition compound.

In another aspect, provided herein is a method for preparing a cycloaddition compound from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (I) catalyst; and passing the solution containing the alkyne component and the azide component through the gravity column; wherein upon contact with the copper (I) catalyst within the matrix, the alkyne component and the azide component react to form the cycloaddition compound.

In another aspect, provided herein is a method for preparing a cycloaddition compound from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (II) precatalyst and a reducing agent; wherein a copper (I) catalyst is generated from the reduction of the copper (II) precatalyst with the reducing agent; and passing the solution containing the alkyne component and the azide component through the gravity column; wherein upon contact with the copper (I) catalyst within the matrix, the alkyne component and the azide component react to form the cycloaddition compound.

In another aspect, provided herein is a method for preparing a cycloaddition compound from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the gravity column; wherein upon contact with the copper (I) catalyst within the matrix, the alkyne component and the azide component react to form the cycloaddition compound.

In some embodiments, the alkyne component and/or the azide component comprises a small molecule, a protein, a peptide, an amino acid, an oligonucleotide, a nucleotide, a nucleoside, a carbohydrate, or a fluorophore. In some embodiments, the alkyne component comprises a small molecule, a protein, a peptide, an amino acid, an oligonucleotide, a nucleotide, a nucleoside, a carbohydrate, or a fluorophore. In some embodiments, the azide component comprises a small molecule, a protein, a peptide, an amino acid, an oligonucleotide, a nucleotide, a nucleoside, a carbohydrate, or a fluorophore. In some embodiments, the alkyne component comprises an oligonucleotide and the azide component comprises a carbohydrate. In some embodiments, the alkyne component comprises a peptide and the azide component comprises a fluorophore. In some embodiments, the alkyne component and/or the azide component contains cells and/or cell lysates. In some embodiments, the alkyne component and/or the azide component contains cells. In some embodiments, the alkyne component and/or the azide component contains cell lysates. In some embodiments, the alkyne component contains cells. In some embodiments, the azide component contains cells. In some embodiments, the alkyne component contains cell lysates. In some embodiments, the azide component contains cell lysates.

In another aspect, provided herein is a method for preparing a glycosylated DNA from a reaction catalyzed by a heterogeneous copper catalyst, comprising mixing an alkynyl DNA component and an azido carbohydrate component in an appropriate solvent to form a solution; transferring the solution containing the alkynyl DNA component and the azido carbohydrate component to a centrifuge column with a matrix barrier at the bottom of the centrifuge column; wherein the centrifuge column comprises a matrix of a copper (II) precatalyst and a reducing agent; wherein a copper (I) catalyst is generated from the reduction of the copper (II) precatalyst with the reducing agent; and passing the solution containing the alkynyl DNA component and the azido carbohydrate component through the centrifuge column by centrifuging the centrifuge column for a sufficient period of time; wherein upon contact with the copper (I) catalyst within the matrix, the alkynyl DNA component and the azido carbohydrate component react to form a glycosylated DNA.

In another aspect, provided herein is a method for preparing a fluorescent labeled peptide from a reaction catalyzed by a heterogeneous copper catalyst, comprising mixing an alkynyl peptide component and an azido fluorogenic dye component in an appropriate solvent to form a solution; transferring the solution containing the alkynyl peptide component and the azido fluorogenic dye component to a centrifuge column with a matrix barrier at the bottom of the centrifuge column; wherein the centrifuge column comprises a matrix of copper (II) precatalyst and a reducing agent; wherein a copper (I) catalyst is generated from the reduction of the copper (II) precatalyst with the reducing agent; and passing the solution containing the alkynyl peptide component and the azido fluorogenic dye component through the centrifuge column by centrifuging the centrifuge column for a sufficient period of time; wherein upon contact with the copper (I) catalyst within the matrix, the alkynyl peptide component and the azido fluorogenic component react to form a fluorescent labeled peptide.

In some embodiments, the cycloaddition compound, glycosylated DNA, or fluorescent labeled peptide is eluted with an appropriate buffer solution followed by centrifuging the centrifuge column for a sufficient period of time. In some embodiments, the cycloaddition compound is eluted with an appropriate buffer solution followed by centrifuging the centrifuge column for a sufficient period of time. In some embodiments, glycosylated DNA is eluted with an appropriate buffer solution followed by centrifuging the centrifuge column for a sufficient period of time. In some embodiments, the fluorescent labeled peptide is eluted with an appropriate buffer solution followed by centrifuging the centrifuge column for a sufficient period of time.

In some embodiments, the cycloaddition compound, glycosylated DNA, or fluorescent labeled peptide is a 1,2,3-triazole. In some embodiments, the cycloaddition compound is a 1,2,3-triazole. In some embodiments, the glycosylated DNA is a 1,2,3-triazole. In some embodiments, the fluorescent labeled peptide is a 1,2,3-triazole.

In some embodiments, the cycloaddition compound, glycosylated DNA, or fluorescent labeled peptide is a cell lysate derivatized product. In some embodiments, the cell lysate derivatized product is free or substantially free of impurities derived from cells and/or cell lysates. In some embodiments, the impurities include but are not limited to proteins and related materials derived from cells and/or cell lysates that are able to pass through the column matrix. In some embodiments, the cell lysate derivatized product requires secondary purification to remove trace impurities derived from cells and/or cell lysates. In some embodiments, the cell lysate derivatized product is free or substantially free of impurities derived from cell lysates. In some embodiments, the impurities include but are not limited to proteins and related materials derived from cell lysates that are able to pass through the column matrix. In some embodiments, the cell lysate derivatized product requires secondary purification to remove trace impurities derived from cell lysates. In some embodiments, secondary purification is any one of the methods disclosed herein for additional purification.

In some embodiments, the method further comprises passing the solution containing the cycloaddition compound, glycosylated DNA, or fluorescent labeled peptide through an additional matrix. In some embodiments, the method further comprises passing the solution containing the cycloaddition compound through an additional matrix. In some embodiments, the method further comprises passing the solution containing the glycosylated DNA through an additional matrix. In some embodiments, the method further comprises passing the solution containing the fluorescent labeled peptide through an additional matrix.

In certain embodiments, the additional matrix is a resin suitable for the purification of the cycloaddition compound, glycosylated DNA or fluorescent labeled peptide. In certain embodiments, the additional matrix is a resin suitable for the purification of the cycloaddition compound. In certain embodiments, the additional matrix is a resin suitable for the purification of the glycosylated DNA. In certain embodiments, the additional matrix is a resin suitable for the purification of the fluorescent labeled peptide. In certain embodiments, the additional matrix is a size-exclusion resin.

In some embodiments, the method further comprises passing the solution containing the cycloaddition compound, glycosylated DNA, or fluorescent labeled peptide through an additional matrix that is a resin suitable for the purification of the cycloaddition compound, glycosylated DNA, or fluorescent labeled peptide. In some embodiments, the method further comprises passing the solution containing the cycloaddition compound through an additional matrix that is a resin suitable for the purification of the cycloaddition compound. In some embodiments, the method further comprises passing the solution containing the glycosylated DNA through an additional matrix that is a resin suitable for the purification of the glycosylated DNA. In some embodiments, the method further comprises passing the solution containing the fluorescent labeled peptide through an additional matrix that is a resin suitable for the purification of the fluorescent labeled peptide. In certain embodiments, the additional matrix is a size-exclusion resin.

In some embodiments, the matrix further comprises an ion-exchange resin. In certain embodiments, the ion-exchange resin is an anion exchange resin or a cation exchange resin. In some embodiments, the column, centrifuge column, or gravity column further comprises a size-exclusion resin.

In some embodiments, the column further comprises a size-exclusion resin. In some embodiments, the centrifuge column further comprises a size-exclusion resin. In some embodiments, the gravity column further comprises a size-exclusion resin.

In some embodiments, the copper (II) precatalyst further comprises a ligand. In some embodiments, the reducing agent is zinc amalgam. In some embodiments, the method is suitable for use in microspin column chromatography.

In one aspect, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (I) catalyst; and passing the solution containing the alkyne component and the azide component through the column; wherein upon contact with the copper (I) catalyst within the matrix, the alkyne component and the azide component react to form the cell lysate derivatized product.

In another aspect, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (II) precatalyst and a reducing agent; wherein a copper (I) catalyst is generated from the reduction of the copper (II) precatalyst with the reducing agent; and passing the solution containing the alkyne component and the azide component through the column; wherein upon contact with the copper (I) catalyst within the matrix, the alkyne component and the azide component react to form the cell lysate derivatized product.

In another aspect, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the column; wherein upon contact with the copper (I) catalyst within the matrix, the alkyne component and the azide component react to form the cell lysate derivatized product.

In some embodiments, the column is suitable use in gravity column chromatography or centrifugal column chromatography. In some embodiments, passing the solution containing the alkyne component and the azide component through the column is through gravity. In certain embodiments, passing the solution containing the alkyne component and the azide component through the column further comprises the use of positive pressure from air or a compressed gas. In some embodiments, passing the solution containing the alkyne component and the azide component through the column is through centrifuging the column for a sufficient period of time.

In another aspect, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (I) catalyst; and passing the solution containing the alkyne component and the azide component through the centrifuge column by centrifuging the centrifuge column for a sufficient period of time; wherein upon contact with the copper (I) catalyst within the matrix, the alkyne component and the azide component react to form the cell lysate derivatized product.

In another aspect, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (II) precatalyst and a reducing agent; wherein a copper (I) catalyst is generated from the reduction of the copper (II) precatalyst with the reducing agent; and passing the solution containing the alkyne component and the azide component through centrifuge column by centrifuging the centrifuge column for a sufficient period of time; wherein upon contact with the copper (I) catalyst within the matrix, the alkyne component and the azide component react to form the cell lysate derivatized product.

In another aspect, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the centrifuge column by centrifuging the centrifuge column for a sufficient period of time; wherein upon contact with the copper (I) catalyst within the matrix, the alkyne component and the azide component react to form the cell lysate derivatized product.

In another aspect, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (I) catalyst; and passing the solution containing the alkyne component and the azide component through the gravity column; wherein upon contact with the copper (I) catalyst within the matrix, the alkyne component and the azide component react to form the cell lysate derivatized product.

In another aspect, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (II) precatalyst and a reducing agent; wherein a copper (I) catalyst is generated from the reduction of the copper (II) precatalyst with the reducing agent; and passing the solution containing the alkyne component and the azide component through the gravity column; wherein upon contact with the copper (I) catalyst within the matrix, the alkyne component and the azide component react to form the cell lysate derivatized product.

In another aspect, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the gravity column; wherein upon contact with the copper (I) catalyst within the matrix, the alkyne component and the azide component react to form the cell lysate derivatized product.

In some embodiments, the alkyne component and/or the azide component comprises a small molecule, a protein, a peptide, an amino acid, an oligonucleotide, a nucleotide, a nucleoside, a carbohydrate, or a fluorophore. In some embodiments, the alkyne component comprises a small molecule, a protein, a peptide, an amino acid, an oligonucleotide, a nucleotide, a nucleoside, a carbohydrate, or a fluorophore. In some embodiments, the azide component comprises a small molecule, a protein, a peptide, an amino acid, an oligonucleotide, a nucleotide, a nucleoside, a carbohydrate, or a fluorophore. In some embodiments, the alkyne component comprises an oligonucleotide and the azide component comprises a carbohydrate. In some embodiments, the alkyne component comprises a peptide and the azide component comprises a fluorophore. In some embodiments, the alkyne component and/or the azide component contains cells and/or cell lysates. In some embodiments, the alkyne component and/or the azide component contains cells. In some embodiments, the alkyne component and/or the azide component contains cell lysates. In some embodiments, the alkyne component contains cells. In some embodiments, the azide component contains cells. In some embodiments, the alkyne component contains cell lysates. In some embodiments, the azide component contains cell lysates.

In some embodiments, the cell lysate derivatized product is eluted with an appropriate buffer solution followed by centrifuging the centrifuge column for a sufficient period of time. In some embodiments, the cell lysate derivatized product is eluted with an appropriate buffer solution followed by centrifuging the centrifuge column for a sufficient period of time.

In some embodiments, the cell lysate derivatized product is a 1,2,3-triazole. In some embodiments, the cell lysate derivatized product is free or substantially free of impurities derived from cells and/or cell lysates. In some embodiments, the impurities include but are not limited to proteins and related materials derived from cells and/or cell lysates that are able to pass through the column matrix. In some embodiments, the cell lysate derivatized product requires secondary purification to remove trace impurities derived from cells and/or cell lysates. In some embodiments, the cell lysate derivatized product is free or substantially free of impurities derived from cell lysates. In some embodiments, the impurities include but are not limited to proteins and related materials derived from cell lysates that are able to pass through the column matrix. In some embodiments, the cell lysate derivatized product requires secondary purification to remove trace impurities derived from cell lysates. In some embodiments, secondary purification is any one of the methods disclosed herein for additional purification.

In some embodiments, the method further comprises passing the solution containing the cell lysate derivatized product through an additional matrix. In certain embodiments, the additional matrix is a resin suitable for the purification of the cell lysate derivatized product. In certain embodiments, the additional matrix is a size-exclusion resin.

In some embodiments, the method further comprises passing the solution containing the cell lysate derivatized product through an additional matrix that is a resin suitable for the purification of the cell lysate derivatized product. In certain embodiments, the additional matrix is a size-exclusion resin.

In some embodiments, the matrix further comprises an ion-exchange resin. In certain embodiments, the ion-exchange resin is an anion exchange resin or a cation exchange resin. In some embodiments, the column, centrifuge column, or gravity column further comprises a size-exclusion resin. In some embodiments, the column further comprises a size-exclusion resin. In some embodiments, the centrifuge column further comprises a size-exclusion resin. In some embodiments, the gravity column further comprises a size-exclusion resin.

In some embodiments, the copper (II) precatalyst further comprises a ligand. In some embodiments, the reducing agent is zinc amalgam. In some embodiments, the method is suitable for use in microspin column chromatography.

In another aspect, provided herein is a column matrix comprising a heterogeneous metal catalyst. In another aspect, provided herein is a column matrix comprising a heterogeneous metal catalyst that catalyzes the azide-alkyne cycloaddition.

In some embodiments, the column matrix is suitable for catalyzing an azide-alkyne cycloaddition. In some embodiments, the heterogeneous metal catalyst comprises a copper catalyst, a ruthenium catalyst, a silver catalyst, or a zinc catalyst. In some embodiments, the heterogeneous metal catalyst comprises a copper catalyst. In some embodiments, the heterogeneous metal catalyst comprises a ruthenium catalyst. In some embodiments, the heterogeneous metal catalyst comprises a silver catalyst. In some embodiments, the heterogeneous metal comprises a zinc catalyst.

In some embodiments, the copper catalyst further comprises a ligand. In some embodiments, the copper catalyst comprises a copper (II) precatalyst and reducing agent. In some embodiments, the copper (II) precatalyst further comprises a ligand. In some embodiments, the reducing agent is zinc amalgam.

In another aspect, provided herein is a column matrix comprising a heterogeneous copper catalyst. In another aspect, provided herein is a column matrix comprising a heterogeneous copper catalyst that catalyzes the azide-alkyne cycloaddition.

In some embodiments, the heterogeneous copper catalyst further comprises a ligand. In some embodiments, the heterogeneous copper catalyst comprises a copper (II) precatalyst and reducing agent. In some embodiments, the copper (II) precatalyst further comprises a ligand. In some embodiments, the reducing agent is zinc amalgam.

In another aspect, provided herein is a column matrix comprising a copper (I) catalyst. In another aspect, provided herein is a column matrix comprising a copper (II) precatalyst and a reducing agent. In another aspect, provided herein is a column matrix comprising a copper (II) precatalyst and zinc amalgam.

In another aspect, provided herein is a column matrix for use in bioconjugation comprising a copper (I) catalyst. In another aspect, provided herein is a column matrix for use in bioconjugation comprising a copper (II) precatalyst and a reducing agent. In another aspect, provided herein is a column matrix for use in bioconjugation comprising a copper (II) precatalyst and zinc amalgam. In another aspect, provided herein is a column matrix for use in bioconjugation catalyzed by a heterogeneous copper catalyst comprising a copper (I) catalyst. In another aspect, provided herein is a column matrix for use in bioconjugation catalyzed by a heterogeneous copper comprising a copper (II) precatalyst and a reducing agent. In another aspect, provided herein is a column matrix for use in bioconjugation catalyzed by a heterogeneous copper comprising a copper (II) precatalyst and zinc amalgam.

In some embodiments, the column matrix further comprises an ion-exchange resin. In certain embodiments, the ion-exchange resin is an anion exchange resin or a cation exchange resin. In some embodiments, the column matrix further comprises a size-exclusion resin. In some embodiments, the column matrix further comprises an additional column matrix. In certain embodiments, the additional column matrix is a resin suitable for the purification of a cycloaddition compound formed by azide-alkyne cycloaddition. In certain embodiments, the additional column matrix is a resin suitable for the purification of a product. In certain embodiments, the product is a triazole formed from a heterogeneous metal-catalyzed azide alkyne cycloaddition. In certain embodiments, the additional column matrix is a size-exclusion resin.

In some embodiments, the column matrix further comprises an additional column matrix that is a resin that is suitable for the purification of a product. In some embodiments, the column matrix further comprises an additional column matrix that is a resin that is suitable for the purification of a product formed from the azide-alkyne cycloaddition. In certain embodiments, the additional column matrix is a size-exclusion resin.

In some embodiments, the copper (II) precatalyst further comprises a ligand. In some embodiments, the reducing agent is zinc amalgam. In some embodiments, the column matrix is suitable for use in gravity column chromatography or in centrifugal column chromatography. In some embodiments, the column matrix is suitable for use in gravity column chromatography. In some embodiments, the column matrix is suitable for use in centrifugal column chromatography. In certain embodiments, the column matrix is suitable for use in microspin column chromatography. In some embodiments, the column matrix is suitable for use in azide-alkyne cycloaddition.

In another aspect, provided herein is a column comprising a matrix of a heterogeneous metal catalyst. In another aspect, provided herein is a column comprising a matrix of a heterogeneous metal catalyst that catalyzes the azide-alkyne cycloaddition.

In some embodiments, the heterogeneous metal catalyst comprises a copper catalyst, a ruthenium catalyst, a silver catalyst, or a zinc catalyst. In some embodiments, the heterogeneous metal catalyst comprises a copper catalyst. In some embodiments, the heterogeneous metal catalyst comprises a ruthenium catalyst. In some embodiments, the heterogeneous metal catalyst comprises a silver catalyst. In some embodiments, the heterogeneous metal comprises a zinc catalyst.

In some embodiments, the copper catalyst further comprises a ligand. In some embodiments, the copper catalyst comprises a copper (II) precatalyst and a reducing agent. In some embodiments, the copper (II) precatalyst further comprises a ligand. In some embodiments, the reducing agent is zinc amalgam.

In another aspect, provided herein is a column comprising a matrix of a heterogeneous copper catalyst. In another aspect, provided herein is a column comprising a matrix of a heterogeneous copper catalyst that catalyzes the azide-alkyne cycloaddition.

In some embodiments, the heterogeneous copper catalyst further comprises a ligand. In some embodiments, the heterogeneous copper catalyst comprises a copper (II) precatalyst and a reducing agent. In some embodiments, the copper (II) precatalyst further comprises a ligand. In some embodiments, the reducing agent is zinc amalgam.

In another aspect, provided herein is a column comprising a matrix of a copper (I) catalyst. In another aspect, provided herein is a column comprising a matrix of a copper (II) precatalyst and a reducing agent. In another aspect, provided herein is a column comprising a matrix of a copper (II) precatalyst and zinc amalgam.

In another aspect, provided herein is a column for use in bioconjugation comprising a matrix of a copper (I) catalyst. In another aspect, provided herein is a column for use in bioconjugation comprising a matrix of a copper (II) precatalyst and a reducing agent. In another aspect, provided herein is a column for use in bioconjugation comprising a matrix of a copper (II) precatalyst and zinc amalgam. In another aspect, provided herein is a column for use in bioconjugation catalyzed by a heterogeneous copper catalyst comprising a matrix of a copper (I) catalyst. In another aspect, provided herein is a column for use in bioconjugation catalyzed by a heterogeneous copper catalyst comprising a matrix of a copper (II) precatalyst and a reducing agent. In another aspect, provided herein is a column for use in bioconjugation catalyzed by a heterogeneous copper catalyst comprising a matrix of a copper (II) precatalyst and zinc amalgam.

In some embodiments, the matrix further comprises an ion-exchange resin. In some embodiments, the ion-exchange resin is an anion exchange resin or a cation exchange resin. In some embodiments, the matrix further comprises a size-exclusion resin. In some embodiments, the column further comprises an additional matrix. In certain embodiments, the additional matrix is a resin suitable for the purification of a cycloaddition compound formed from an azide-alkyne cycloaddition. In certain embodiments, the additional matrix is a resin suitable for the purification of a product. In certain embodiments, the product is a triazole formed from a heterogeneous metal-catalyzed azide-alkyne cycloaddition. In certain embodiments, the additional matrix is a size-exclusion resin.

In some embodiments, the column further comprises an additional matrix that is a resin suitable for the purification of a cycloaddition compound formed from the azide-alkyne cycloaddition.

In some embodiments, the copper (II) precatalyst further comprises a ligand. In some embodiments, the reducing agent is zinc amalgam. In some embodiments, the column is a gravity column or a centrifuge column. In certain embodiments, the column is a centrifuge column. In certain embodiments, the column is a gravity column. In some embodiments, the centrifuge column is suitable for use in microspin column chromatography. In some embodiments, the column is suitable for use in azide-alkyne cycloaddition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
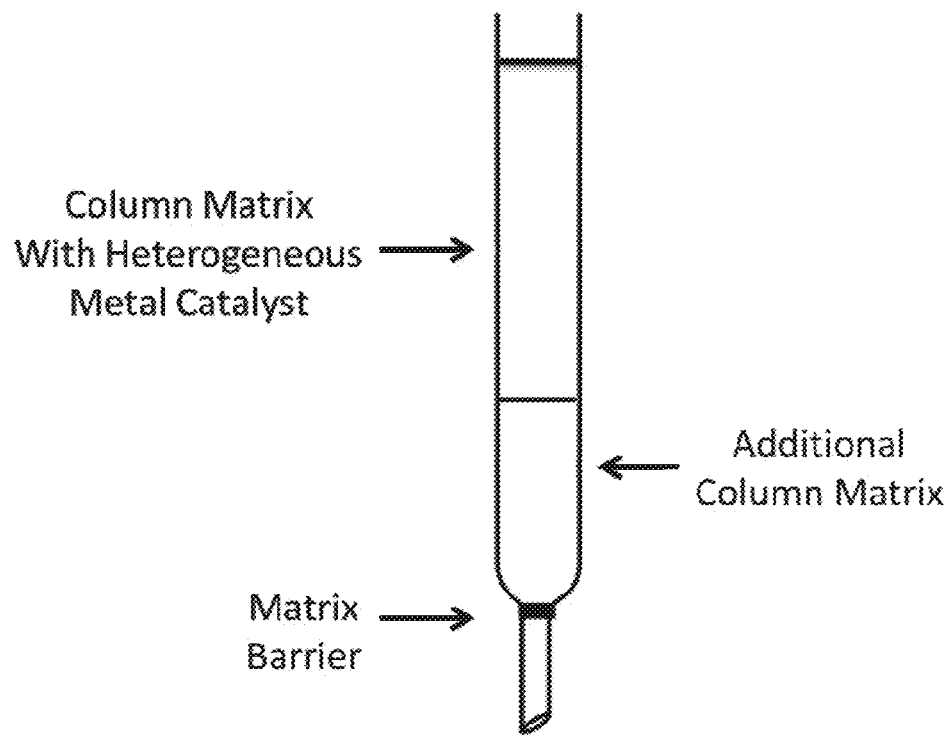
FIG. 1 depicts a schematic diagram of a particular embodiment of the column, wherein the column comprises a matrix comprising a heterogeneous metal catalyst and the column further comprises an additional matrix.

An emerging field has been in developing azide-alkyne cycloaddition processes that use heterogeneous metal catalysts as the advantages of heterogeneous metal systems include easy product separation, minimal waste generation during catalyst separation, catalyst recyclability, and facile catalyst removal. Described herein are methods, compositions and kits utilizing heterogeneous metal catalysts, in particular copper catalysts, for the preparation of compounds, such as triazoles from an azide-alkyne cycloaddition and includes biomolecules.

"Click chemistry" reactions are a set of highly reliable and selective reactions that allow for the rapid synthesis of new compounds. One of the most well-known click reactions is the Huisgen [3+2] azide-alkyne cycloaddition. This reaction has the following advantages: the reaction is generally high yielding and robust; the alkyne and azide components are incorporated into a wide range of substrates; and the triazole formed is essentially chemically inert to reactive conditions. Furthermore, as the azide moiety is not present in naturally existing compounds, the application of the azide-alkyne cycloaddition is of particular interest in bioconjugation.

In the absence of a catalyst, the Huisgen [3+2] azide-alkyne reaction proceeds slowly, usually requires high temperatures or pressures, and yields a mixture of 1,4- and 1,5-triazoles, all of which render this reaction generally unsuitable for most applications involving biomolecules. Transition metals, in particular copper catalysts, have been found to accelerate the azide-alkyne reaction through a different mechanism and allows for the reaction to proceed under aqueous conditions and at room temperature. Although, non-transition metal catalyzed variants of the azide-alkyne reaction, which rely on ring strain rather than transition metal catalysts, have been developed, these methods often require multistep and lengthy syntheses to prepare the necessary reactants. As such, transition metal-catalyzed azide-alkyne cycloaddition, in particular the copper-catalyzed azide-alkyne cycloaddition (CuAAC), has seen widespread use.

Previously, Hong et. al. described a modified procedure for a homogeneous copper-catalyzed azide-alkyne cycloaddition that provided a general straightforward approach for bioconjugation (See Hong et al., *Angew. Chem. Int. Ed.* 2009, 48, 9879-9883 and Hong et al., *ChemBioChem*, 2008, 9, 1481-1486). The new protocol provided some important improvements—most notably, being able to run the reaction in air instead of anaerobically; however, a key drawback remaining is the removal of added reagents, such as ascorbic acid, aminoguanidine, and the copper-ligand catalyst complex.

The use of a heterogeneous catalyst for azide-alkyne cycloaddition is an attractive alternative. A heterogeneous catalyst allows for easy product separation, minimal waste generation during catalyst separation, catalyst recyclability, and facile catalyst removal. Furthermore, a heterogeneous catalyst is especially advantageous for use in biological applications since one of the advantages of a heterogeneous system is facile removal of the catalyst, which is important especially given the cytotoxic properties of certain transition metals, especially copper. Despite these advantages, heterogeneous metal catalysts that have been employed for azide-alkyne cycloaddition still suffer from significant disadvantages. Some of them include multi-step catalyst preparation, low loading, long reaction times, harsh reaction conditions, tedious work up of the catalyst and products. All of which limit the utility of a heterogeneous metal catalyst in bioconjugation and for use with biomolecules.

Described herein are methods for using a heterogeneous metal catalyst, such as copper, for the azide-alkyne cycloaddition. Such methods are used to both synthesize and purify cycloaddition compounds (e.g., triazoles), including biomolecules, in essentially one step with the use of a chromatography column that contains a matrix comprising a heterogeneous metal catalyst. In the methods described herein, a solution containing the alkyne component and azide component is passed through a column containing a matrix comprising the heterogeneous metal catalyst, wherein upon passing the solution through the column by either gravity or centrifugation, the alkyne component and azide component react upon contact with the heterogeneous metal catalyst in the matrix to form a triazole product. In some embodiments, the method further comprises passing the triazole product through an additional matrix. In some embodiments, the additional matrix is a resin that allows for purification of the triazole product. In some embodiments, the method further comprises passing the triazole product through an additional matrix that is a resin that allows for the purification of the triazole product. In some embodiments, the column is suitable for use in gravity column chromatography or in centrifugal chromatography.

In some of the methods provided herein, the heterogeneous metal catalyst is a metal catalyst that catalyzes the azide-alkyne cycloaddition. Examples of such heterogeneous metal catalysts include but are not limited to copper, ruthenium, silver and zinc. In some of the methods provided herein, the heterogeneous metal catalyst comprises a copper catalyst. In some of the methods provided herein, the heterogeneous copper catalyst comprises a copper (I) catalyst. In some of the methods provided herein, the heterogeneous copper catalyst comprises a copper (II) precatalyst and a reducing agent, wherein the copper (I) catalyst is generated from the reduction of the copper (II) precatalyst. In some of the methods provided herein, the reducing agent is zinc amalgam.

One of the advantages of the methods disclosed herein is that these methods are useful to chemically modify a wide range of cycloaddition compounds, including small molecules and biomolecules. Furthermore, in some embodiments, these methods are performed under aqueous conditions and at room temperature. The chemical modification of biomolecules, such as proteins, nucleic acids, and carbohydrates, is particularly advantageous, and the methods disclosed herein allow for facile bioconjugation through a one-step synthesis and purification process. The use of the disclosed matrix comprising the heterogeneous metal catalyst is particularly well suited for bioconjugation as it offers facile product separation and catalyst removal. Also in some embodiments, the use of the disclosed matrix comprising the heterogeneous metal catalyst for bioconjugation also allows for the purification from cells and cell lysates, wherein the alkyne component and/or azide component contain cells and/or cell lysates. In some embodiments, the matrix disclosed herein does not allow for the bulk of the cells and/or cell lysates to pass through, thereby affording a product that is free or substantially free of impurities derived from cells and/or cell lysates. Also disclosed herein are methods for preparing glycosylated DNA and fluorescent labeled peptides. Furthermore, compositions and kits related to the methods disclosed herein are also described.

DEFINITIONS

As used herein "alkyne" or "alkynyl" refers to a compound containing a carbon-carbon triple bond functional group. In some embodiments, alkyne or alkynyl refers to a compound containing a mono-substituted or terminal alkyne. In some embodiments, alkyne or alkynyl refers to a compound containing a di-substituted or internal alkyne.

As used herein "azide" or "azido" refers to a compound containing the anion $N_3^-$, wherein N is nitrogen.

As used herein "column" refers to a tube that is used for the separation of compounds (e.g., cycloaddition compounds) by passing the compounds through a matrix packed within the column in the presence of a suitable solvent or buffer solution under gravity or centrifugal force. Such columns are further equipped with a matrix barrier, which is at the bottom of the tube and is used to contain the matrix packed within the column. In some embodiments, the matrix barrier is a frit with a nominal pore size. In some embodiments, the matrix barrier is a membrane filter. In some embodiments, the matrix barrier is a cotton or glass wool plug. As used herein, columns are synonymous with chromatography columns and encompass any type of means to pass any suitable solvent, solution, or buffer solution through the column, such as gravity or centrifugal force.

As used herein "centrifuge column" refers to a tube that is used for the separation of compounds (e.g., cycloaddition compounds), which include biomolecules, by passing the compounds through a matrix packed within the column in the presence of a suitable solvent or buffer under centrifugal force. Such centrifuge columns are further equipped with a matrix barrier, which is at the bottom of the tube and is used to contain the matrix packed within the column. In some embodiments, the matrix barrier is a frit with a nominal pore size. In some embodiments, the matrix barrier is a membrane filter. As used herein, centrifuge columns are synonymous with spin columns and encompass any sample volume and type capable of being separated by centrifugal force.

As used herein "gravity column" refers to a tube that is used for the separation of compounds (e.g., cycloaddition compounds), which include biomolecules, by passing the compounds through a matrix packed within the column in the presence of a suitable solvent or buffer under gravity. In some embodiments, the flow of the solvent or buffer is facilitated with the use of positive pressure from air or compressed gas, e.g., flash chromatography. Such gravity columns are further equipped with a matrix barrier, which is at the bottom of the tube and is used to contain the matrix packed within the column. In some embodiments, the matrix barrier is a frit with a nominal pore size. In some embodiments, the matrix barrier is a cotton or glass wool plug. As used herein, gravity columns encompass any sample volume and type capable of being separated by gravity force and optionally, positive pressure from air or compressed gas.

As used herein, the Huisgen 1,3 dipolar cycloaddition of azides and alkynes refers to the reaction between an azide or a terminal or internal alkyne to yield a 1,2,3 triazole. In some embodiments, the reaction yields 1,4-disubstituted [1,2,3]-triazoles, 1,5-disubstituted [1,2,3]-triazoles, or a mixture thereof.

As used herein "copper-catalyzed azide-alkyne cycloaddition" refers to the Huisgen 1,3-dipolar cycloaddition of azides and alkynes catalyzed by copper (I). In some embodiments, the copper-catalyzed azide-alkyne cycloaddition leads to the formation of 1,4-disubstituted [1,2,3]-triazoles. In some embodiments, the copper-catalyzed azide-alkyne cycloaddition leads to the formation of 1,5-disubstituted [1,2,3]-triazoles. Synonyms include, but are not limited to, copper-catalyzed azide-alkyne coupling, copper-catalyzed azide-alkyne click reaction, copper-catalyzed click chemistry, and copper-catalyzed azide-alkyne Huisgen [3+2] cycloaddition.

As used herein "metal-catalyzed azide-alkyne cycloaddition" refers to the Huisgen 1,3-dipolar cycloaddition of azides and alkynes catalyzed by a transition metal capable of catalyzing the azide-alkyne cycloaddition. Examples of such metals include but are not limited to copper, silver, ruthenium, and zinc. In some embodiments, the metal-catalyzed azide-alkyne cycloaddition leads to the formation of 1,4-disubstituted [1,2,3]-triazoles. In some embodiments, the metal-catalyzed azide-alkyne cycloaddition leads to the formation of 1,5-disubstituted [1,2,3]-triazoles. Synonyms include, but are not limited to, metal-catalyzed azide-alkyne coupling, metal-catalyzed azide-alkyne click reaction, metal-catalyzed click chemistry, and metal-catalyzed azide-alkyne Huisgen [3+2] cycloaddition. In some embodiments, the "metal-catalyzed azide-alkyne cycloaddition" is synonymous with heterogeneous metal-catalyzed azide-alkyne cycloaddition or heterogeneous transition metal-catalyzed azide-alkyne cycloaddition.

As used herein "copper (0) precatalyst" is meant to encompass any suitable copper (0) source that is capable of being oxidized by an oxidizing agent to form a catalytically active copper (I) species. This catalytically active copper (I) species facilitates the copper-catalyzed azide-alkyne cycloaddition reaction.

As used herein "copper (II) precatalyst" is meant to encompass any suitable copper (II) salt or copper (II) metal-ligand complex that is capable of being reduced by a reducing agent to form a catalytically active copper (I) species. This catalytically active copper (I) species facilitates the copper-catalyzed azide-alkyne cycloaddition reaction.

As used herein "copper (I) catalyst" is meant to encompass any suitable copper (I) salt or copper (I) metal-ligand complex that is capable of catalyzing the azide-alkyne cycloaddition reaction.

As used herein, an "azide component" is meant to encompass any compound, including any small molecule and biomolecule, that contains an azide component that is able to react with an alkyne component to form a [1,2,3]-triazole. In some embodiments, the azide component is generated in situ with a suitable azide reagent, such as sodium azide.

As used herein, an "alkyne component" is meant to encompass any compound, including any small molecule or biomolecule, that contains an alkyne component that is able to react with an azide component to form a 1,2,3-triazole.

As used herein, an "ion-exchange resin" is meant to encompass an insoluble matrix or support structure that is capable of trapping of ions with concomitant releasing of other ions. The counterions within the resin are mobile and are exchangeable with other counterions while ions of the same charge type are not mobile and remain bound to the resin. Ion-exchange resins are optionally classified based on the charge of the exchangeable ions. For example, cation-exchange resins are resins that have positively charged mobile ions available for exchange. Anion-exchange resins are resins that have negatively charged mobile ions available for exchange. Additionally, in some embodiments, ion-exchange resins are a combination of cation-exchange and anion-exchange resins. These resins are optionally further classified by the ionic strength of the bound ion, such as strong or weak exchange resins.

As used herein, a "size-exclusion resin" is meant to encompass an insoluble matrix or support structure that capable or separating molecules based on molecular size. The term "gel-filtration resin" is synonymous with size-exclusion resin.

As used herein, a "cell lysate derivatized product" refers to a compound that is prepared through the metal catalyzed azide-alkyne cycloaddition disclosed herein, wherein the alkyne component and/or azide component contains cells and/or cell lysates. When the solution containing the alkyne component and azide component and cells and/or cell lysates is passed through any one of the columns described herein, the majority of the cells and/or cell lysates remain at the top of the column and do not pass through, thereby providing a cell lysate derivatized product, e.g bioconjugated product, that is free or substantially free of impurities derived from the cells and/or cell lysates. In some instances, the cell lysate derivatized product contains trace impurities derived from the cells and/or cell lysates and require further purification to remove these impurities. These impurities include but are not limited to proteins and related materials that are derived from cells and/or cell lysates that are soluble and are able to pass through any one of the column matrices described herein.

As used herein "free or substantially free" in reference to a particular compound refers that the amount of said compound is present in about 10 ppm or less. In some instances, the said compound is present in about 5 ppm or less. In some instances, the compound is present in about 1 ppm or less.

Methods

The methods disclosed herein encompass the synthesis and purification of cycloaddition compounds, including biomolecules, prepared through the heterogeneous metal-catalyzed azide-alkyne cycloaddition utilizing a matrix comprising a heterogeneous metal catalyst. The matrix is contained within a column, a tube that contains a matrix barrier at the bottom of the column. The matrix barrier is used to contain the matrix within the column. In some instances, the matrix barrier is a frit with a nominal pore size. In other instances, the matrix barrier is a membrane filter. In other instances, the matrix barrier is a cotton or glass wool plug. These methods allow for the addition of the reactive components—the addition of the alkyne containing compound and the azide containing compound to the column. Immobilization of the alkyne and azide components on to the matrix is accomplished through passing the solution containing the alkyne and azide components under gravity or centrifugal force, wherein upon contact with the heterogeneous metal catalyst within the matrix, the alkyne and azide react to form the triazole product. The triazole product is then eluted with an appropriate buffer solution, solvent, or solution. In some embodiments, purification is achieved by incorporating an additional matrix to the column such that once the triazole product has been formed in matrix comprising that heterogeneous metal catalyst, the triazole product is eluted through the additional matrix comprising a resin suitable for further purifying the product, such as a size-exclusion resin.

In some embodiments, the triazole is a cell lysate derivatized product. In some embodiments, the cell lysate derivatized product is free or substantially free of impurities derived from cells and/or cell lysates. In some embodiments, the impurities include but are not limited to proteins and related materials derived from cells and/or cell lysates that are able to pass through the column matrix. In some embodiments, the cell lysate derivatized product requires secondary purification to remove trace impurities derived from cells and/or cell lysates. In some embodiments, the cell lysate derivatized product is free or substantially free of impurities derived from cell lysates. In some embodiments, the impurities include but are not limited to proteins and related materials derived from cell lysates that are able to pass through the column matrix. In some embodiments, the cell lysate derivatized product requires secondary purification to remove trace impurities derived from cell lysates. In some embodiments, secondary purification is any one of the methods disclosed herein for additional purification.

The heterogeneous metal catalyst for these methods described herein comprises a heterogeneous metal catalyst that is suitable for catalyzing the azide-alkyne cycloaddition. Examples of such heterogeneous metals catalysts include, but are not limited to, copper, ruthenium, silver and zinc.

Provided herein is a method for preparing a cycloaddition compound (e.g., a triazole from the azide-alkyne cycloaddition) from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (I) catalyst; and passing the solution containing the alkyne component and the azide component through the column; wherein upon contact with the copper (I) catalyst within the matrix, the alkyne component and the azide component react to form the cycloaddition compound.

Also provided herein is a method for preparing a cycloaddition compound (e.g., a triazole from the azide-alkyne cycloaddition) from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (II) precatalyst and a reducing agent; wherein a copper (I) catalyst is generated from the reduction of the copper (II) precatalyst with the reducing agent; and passing the solution containing the alkyne component and the azide component through the column; wherein upon contact with the copper (I) catalyst within the matrix, the alkyne component and the azide component react to form the cycloaddition compound. In some embodiments, the reducing agent is zinc amalgam.

Additionally, provided herein is a method for preparing a cycloaddition compound (e.g., a triazole from the azide-alkyne cycloaddition) from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the column; wherein upon contact with the copper (I) catalyst within the matrix, the alkyne component and the azide component react to form the cycloaddition compound.

In some embodiments, the column is suitable for use in gravity column chromatography or centrifugal column chromatography. In some embodiments, passing the solution containing the alkyne component and the azide component through the column is through gravity. In further embodiments, passing the solution containing the alkyne component and the azide component through the column further comprises the use of positive pressure from air or a compressed gas. In some embodiments, passing the solution containing the alkyne component and the azide component through the column is through centrifuging the column for a sufficient period of time.

In some embodiments, the column further comprises an additional matrix. In some embodiments, the column further comprises an additional matrix suitable for purification of the cycloaddition compound. In some embodiments, the additional matrix is a resin. In some embodiments, the column further comprises a resin suitable for purification of the product. In some embodiments, the resin is size-exclusion resin. In some embodiments, the column further comprises a resin. In some embodiments, the column further comprises a resin suitable for the purification of the cycloaddition compound. In some embodiments, the resin is size-exclusion resin.

In some embodiments, the column further comprises an additional matrix that is a resin suitable for the purification of the cycloaddition compound. In some embodiments, the resin is size-exclusion resin.

In some embodiments, the cycloaddition compound is eluted with an appropriate solvent. In some embodiments, the cycloaddition compound is eluted with an appropriate solvent by passing the solvent through the column through gravity. In some embodiments, wherein the cycloaddition compound is eluted with an appropriate solvent by passing the solvent through the column through gravity, positive pressure from air or compressed gas is also used to facilitate solvent flow. In some embodiments, the cycloaddition compound is eluted with an appropriate solvent by passing the solvent through the column through centrifugation. In some embodiments, the cycloaddition compound is eluted with an appropriate buffer solution. In some embodiments, the cycloaddition compound is eluted with an appropriate buffer solution by passing the buffer solution through the column through gravity. In some embodiments, wherein the cycloaddition compound is eluted with an appropriate buffer solution by passing the buffer solution through the column through gravity, positive pressure from air or compressed gas is also used to facilitate solvent flow. In some embodiments, the cycloaddition compound is eluted with an appropriate buffer solution by passing the buffer solution through the column through centrifugation.

Provided herein is a method for preparing a cycloaddition compound from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (I) catalyst; and passing the solution containing the alkyne component and the azide component through the gravity column; wherein upon contact with the copper (I) catalyst within the matrix, the alkyne component and the azide component react to form the cycloaddition compound.

Also, provided herein is a method for preparing a cycloaddition compound (e.g., a triazole from the azide-alkyne cycloaddition) from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (II) precatalyst and a reducing agent; wherein a copper (I) catalyst is generated from the reduction of the copper (II) precatalyst with the reducing agent; and passing the solution containing the alkyne component and the azide component through the gravity column; wherein upon contact with the copper (I) catalyst within the matrix, the alkyne component and the azide component react to form the cycloaddition compound.

Also, provided herein is a method for preparing a cycloaddition compound (e.g., a triazole from the azide-alkyne cycloaddition) from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the gravity column; wherein upon contact with the copper (I) catalyst within the matrix, the alkyne component and the azide component react to form the cycloaddition compound.

In some embodiments, the cycloaddition compound is eluted with an appropriate solvent with the use of positive pressure from air or a compressed gas to facilitate solvent flow.

In some embodiments, the method further comprises passing the solution containing the cycloaddition compound through an additional matrix. In some embodiments, the additional matrix is a resin suitable for the purification of the cycloaddition compound. In some embodiments, the method further comprises pass the solution containing the compound through an additional matrix that is suitable for the purification of the cycloaddition compound. In some embodiments, the additional matrix is a size-exclusion matrix. In some embodiments, the solution containing the alkyne component and azide component is aqueous.

Provided herein is a method for preparing a cycloaddition compound (e.g., a triazole from the azide-alkyne cycloaddition) from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (I) catalyst; and passing the solution containing the alkyne component and the azide component through the centrifuge column by centrifuging the centrifuge column for a sufficient period of time; wherein upon contact with the copper (I) catalyst within the matrix, the alkyne component and the azide component react to form the cycloaddition compound.

Also provided herein is a method for preparing a cycloaddition compound (e.g., a triazole from the azide-alkyne cycloaddition) from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (II) precatalyst and a reducing agent; wherein a copper (I) catalyst is generated from the reduction of the copper (II) precatalyst with the reducing agent; and passing the solution containing the alkyne component and the azide component through centrifuge column by centrifuging the centrifuge column for a sufficient period of time; wherein upon contact with the copper (I) catalyst within the matrix, the alkyne component and the azide component react to form the cycloaddition compound. In some embodiments, the reducing agent is zinc amalgam.

Additionally, provided herein is a method for preparing a cycloaddition compound (e.g., a triazole from the azide-alkyne cycloaddition) from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the centrifuge column by centrifuging the centrifuge column for a sufficient period of time; wherein upon contact with the copper (I) catalyst within the matrix, the alkyne component and the azide component react to form the cycloaddition compound.

In some embodiments, the cycloaddition compound is eluted with an appropriate buffer solution followed by centrifuging the centrifuge column for a sufficient period of time.

In some embodiments, the method further comprises passing the solution containing the cycloaddition compound through an additional matrix. In some embodiments, the additional matrix is a resin suitable for the purification of the cycloaddition compound. In some embodiments, the method further comprises passing the solution containing the cycloaddition compound through an additional matrix that is a resin suitable for the purification of the cycloaddition compound. In some embodiments, the additional matrix is a size-exclusion matrix. In some embodiments, the solution containing the alkyne component and azide component is aqueous.

In some embodiments, the cycloaddition compound is a cell lysate derivatized product. In some embodiments, the cell lysate derivatized product is free or substantially free of impurities derived from cells and/or cell lysates. In some embodiments, the impurities include but are not limited to proteins and related materials derived from cells and/or cell lysates that are able to pass through the column matrix. In some embodiments, the cell lysate derivatized product requires secondary purification to remove trace impurities derived from cells and/or cell lysates. In some embodiments, the cell lysate derivatized product is free or substantially free of impurities derived from cell lysates. In some embodiments, the impurities include but are not limited to proteins and related materials derived from cell lysates that are able to pass through the column matrix. In some embodiments, the cell lysate derivatized product requires secondary purification to remove trace impurities derived from cell lysates. In some embodiments, secondary purification is any one of the methods disclosed herein for additional purification.

Similarly, the methods disclosed herein allow for the synthesis and purification of cycloaddition compounds, including biomolecules, prepared through the heterogeneous metal-catalyzed azide-alkyne cycloaddition utilizing a matrix comprising a heterogeneous metal catalyst, wherein the alkyne component and/or azide component contain cells and/or cell lysates. In some instances, the alkyne and/or alkyne components contain cell lysates. In some instances, passing the solution containing the alkyne component and azide component through the column allows for the majority of the cells and/or cell lysates to remain on the top of the column and to not pass through, thereby affording a resultant product that is relatively free of impurities derived from cells and/or cell lysates. In some instances, further purification may be required for the resultant product to remove trace impurities.

Provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (I) catalyst; and passing the solution containing the alkyne component and the azide component through the column; wherein upon contact with the copper (I) catalyst within the matrix, the alkyne component and the azide component react to form the cell lysate derivatized product.

Also provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (II) precatalyst and a reducing agent; wherein a copper (I) catalyst is generated from the reduction of the copper (II) precatalyst with the reducing agent; and passing the solution containing the alkyne component and the azide component through the column; wherein upon contact with the copper (I) catalyst within the matrix, the alkyne component and the azide component react to form the cell lysate derivatized product. In some embodiments, the reducing agent is zinc amalgam.

Additionally, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a column with a matrix barrier at the bottom of the column; wherein the column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the column; wherein upon contact with the copper (I) catalyst within the matrix, the alkyne component and the azide component react to form the cell lysate derivatized product.

In some embodiments, the column is suitable for use in gravity column chromatography or centrifugal column chromatography. In some embodiments, passing the solution containing the alkyne component and the azide component through the column is through gravity. In further embodiments, passing the solution containing the alkyne component and the azide component through the column further comprises the use of positive pressure from air or a compressed gas. In some embodiments, passing the solution containing the alkyne component and the azide component through the column is through centrifuging the column for a sufficient period of time.

In some embodiments, the column further comprises an additional matrix. In some embodiments, the column further comprises an additional matrix suitable for purification of the cell lysate derivatized product. In some embodiments, the additional matrix is a resin. In some embodiments, the column further comprises a resin suitable for purification of the product. In some embodiments, the resin is size-exclusion resin. In some embodiments, the column further comprises a resin. In some embodiments, the column further comprises a resin suitable for the purification of the cell lysate derivatized product. In some embodiments, the resin is size-exclusion resin. In some embodiments, the column further comprises an additional matrix that is a resin that is suitable for the purification of the cell lysate derivatized product. In some embodiments, the additional matrix is a size-exclusion resin.

In some embodiments, the cell lysate derivatized product is eluted with an appropriate solvent. In some embodiments, the cell lysate derivatized product is eluted with an appropriate solvent by passing the solvent through the column through gravity. In some embodiments, wherein the cell lysate derivatized product is eluted with an appropriate solvent by passing the solvent through the column through gravity, positive pressure from air or compressed gas is also used to facilitate solvent flow. In some embodiments, the cell lysate derivatized product is eluted with an appropriate solvent by passing the solvent through the column through centrifugation. In some embodiments, the cell lysate derivatized product is eluted with an appropriate buffer solution. In some embodiments, the cell lysate derivatized product is eluted with an appropriate buffer solution by passing the buffer solution through the column through gravity. In some embodiments, wherein the cell lysate derivatized product is eluted with an appropriate buffer solution by passing the buffer solution through the column through gravity, positive pressure from air or compressed gas is also used to facilitate solvent flow. In some embodiments, the cell lysate derivatized product is eluted with an appropriate buffer solution by passing the buffer solution through the column through centrifugation.

Provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (I) catalyst; and passing the solution containing the alkyne component and the azide component through the gravity column; wherein upon contact with the copper (I) catalyst within the matrix, the alkyne component and the azide component react to form the cell lysate derivatized product.

Also, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (II) precatalyst and a reducing agent; wherein a copper (I) catalyst is generated from the reduction of the copper (II) precatalyst with the reducing agent; and passing the solution containing the alkyne component and the azide component through the gravity column; wherein upon contact with the copper (I) catalyst within the matrix, the alkyne component and the azide component react to form the cell lysate derivatized product.

Also, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a gravity column with a matrix barrier at the bottom of the gravity column; wherein the gravity column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the gravity column; wherein upon contact with the copper (I) catalyst within the matrix, the alkyne component and the azide component react to form a cell lysate derivatized product.

In some embodiments, the cell lysate derivatized product is eluted with an appropriate solvent with the use of positive pressure from air or a compressed gas to facilitate solvent flow.

In some embodiments, the method further comprises passing the solution containing the cell lysate derivatized product through an additional matrix. In some embodiments, the additional matrix is a resin suitable for the purification of the cell lysate derivatized product. In some embodiments, the method further comprises passing the solution containing the cell lysate derivatized product through an additional matrix that is a resin suitable for the purification of the cell lysate derivatized product. In some embodiments, the additional matrix is a size-exclusion matrix. In some embodiments, the solution containing the alkyne component and azide component is aqueous.

Provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (I) catalyst; and passing the solution containing the alkyne component and the azide component through the centrifuge column by centrifuging the centrifuge column for a sufficient period of time; wherein upon contact with the copper (I) catalyst within the matrix, the alkyne component and the azide component react to form the cell lysate derivatized product.

Also provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (II) precatalyst and a reducing agent; wherein a copper (I) catalyst is generated from the reduction of the copper (II) precatalyst with the reducing agent; and passing the solution containing the alkyne component and the azide component through centrifuge column by centrifuging the centrifuge column for a sufficient period of time; wherein upon contact with the copper (I) catalyst within the matrix, the alkyne component and the azide component react to form the cell lysate derivatized product. In some embodiments, the reducing agent is zinc amalgam.

Additionally, provided herein is a method for preparing a cell lysate derivatized product from a reaction catalyzed by a heterogeneous copper catalyst, comprising mixing an alkyne component and an azide component in an appropriate solvent to form a solution; transferring the solution containing the alkyne component and the azide component to a centrifuge column with a matrix barrier at the bottom of the centrifuge column; wherein the centrifuge column comprises a matrix of a copper (II) precatalyst and zinc amalgam; wherein a copper (I) catalyst is generated from the reduction of the copper (II) precatalyst with zinc amalgam; and passing the solution containing the alkyne component and the azide component through the centrifuge column by centrifuging the centrifuge column for a sufficient period of time; wherein upon contact with the copper (I) catalyst within the matrix, the alkyne component and the azide component react to form the cell lysate derivatized product.

In some embodiments, the cell lysate derivatized product is eluted with an appropriate buffer solution followed by centrifuging the centrifuge column for a sufficient period of time.

In some embodiments, the method further comprises passing the solution containing the cell lysate derivatized product through an additional matrix. In some embodiments, the additional matrix is a resin suitable for the purification of the cell lysate derivatized product. In some embodiments, the method further comprises passing the solution containing the cell lysate derivatized product through an additional matrix that is a resin suitable for the purification of the cell lysate derivatized product. In some embodiments, the additional matrix is a size-exclusion matrix. In some embodiments, the solution containing the alkyne component and azide component is aqueous.

In some embodiments, the cell lysate derivatized product is free or substantially free of impurities derived from cells and/or cell lysates. In some embodiments, the impurities include but are not limited to proteins and related materials derived from cells and/or cell lysates that are able to pass through the column matrix. In some embodiments, the cell lysate derivatized product requires secondary purification to remove trace impurities derived from cells and/or cell lysates. In some embodiments, the cell lysate derivatized product is free or substantially free of impurities derived from cell lysates. In some embodiments, the impurities include but are not limited to proteins and related materials derived from cell lysates that are able to pass through the column matrix. In some embodiments, the cell lysate derivatized product requires secondary purification to remove trace impurities derived from cell lysates. In some embodiments, secondary purification is any one of the methods disclosed herein for additional purification.

Azide Component

Azide components contemplated for use include any compound, including any biomolecule that contains an azide moiety. Suitable azide components also include compounds that have a functional group, such as a benzyl halide or α-halo ketone that is capable with reacting with an azide reagent, such as sodium azide, to form an azide in situ. The alkyne component is optionally any organic compound, small molecule, nucleic acid, amino acid, carbohydrate, fluorophore, or antibody that contains an alkyne.

In some embodiments, the azide component is an organic compound. In some embodiments, the azide component comprises a small molecule, a nucleic acid, an amino acid, a carbohydrate, a fluorophore, or an antibody. In some embodiments, the azide component comprises a small molecule, a protein, a peptide, an amino acid, an oligonucleotide, a nucleotide, a nucleoside, a carbohydrate, or a fluorophore. In some embodiments, the azide component comprises a small molecule. In some embodiments, the azide component comprises an antibody. In some embodiments, the azide component comprises a protein. In some embodiments, the azide component comprises a peptide. In some embodiments, the azide component comprises an amino acid. In some embodiments, the azide component comprises an oligonucleotide. In some embodiments, the azide component comprises a nucleotide. In some embodiments, the azide component comprises a nucleoside. In some embodiments, the azide component comprises a carbohydrate. In some embodiments, the azide component comprises a fluorophore.

In some embodiments, the azide component contains cells and/or cell lysates. In some embodiments, the azide component contains cells. In some embodiments, the azide component contains cell lysates.

Alkyne Component

Alkyne components contemplated for use include any compound or biomolecule that contains an alkyne moiety. The alkyne component is optionally any organic compound, small molecule, nucleic acid, amino acid, carbohydrate, fluorophore, or antibody that contains an alkyne.

In some embodiments, the alkyne component is an organic compound. In some embodiments, the alkyne component comprises a small molecule, a nucleic acid, an amino acid, a carbohydrate, a fluorophore, or an antibody. In some embodiments, the alkyne component comprises a small molecule, a protein, a peptide, an amino acid, an oligonucleotide, a nucleotide, a nucleoside, a carbohydrate, or a fluorophore. In some embodiments, the alkyne component comprises a small molecule. In some embodiments, the alkyne component comprises an antibody. In some embodiments, the alkyne component comprises a protein. In some embodiments, the alkyne component comprises a peptide. In some embodiments, the alkyne component comprises an amino acid. In some embodiments, the alkyne component comprises an oligonucleotide. In some embodiments, the alkyne component comprises a nucleotide. In some embodiments, the alkyne component comprises a nucleoside. In some embodiments, the alkyne component comprises a carbohydrate. In some embodiments, the alkyne component comprises a fluorophore.

In some embodiments, the alkyne component comprises an oligonucleotide and the azide component comprises a carbohydrate. In some embodiments, the alkyne component comprises a carbohydrate and the azide component comprises an oligonucleotide. In some embodiments, alkyne component comprises a peptide and the azide component comprises a fluorophore.

In some embodiments, the alkyne component contains cells and/or cell lysates. In some embodiments, the alkyne component contains cells. In some embodiments, the alkyne component contains cell lysates.

Azide-Alkyne Cycloaddition

The heterogeneous metal catalyzed cycloaddition or [3+2] of an alkyne component with the azide component forms a [1,2,3]-triazole (also referenced herein as a cycloaddition compound). In some embodiments, the [1,2,3] triazole is a 1,4 disubstituted [1,2,3]-triazole. In some embodiments, the [1,2,3]-triazole is a 1,5-disubstituted [1,2,3]-triazole. In embodiments, the product is a mixture of 1,4 disubstituted [1,2,3]-triazole and 1,5-disubstituted [1,2,3]-triazoles.

The copper-catalyzed cycloaddition or [3+2] of an alkyne component with the azide component forms a [1,2,3]-triazole. In some embodiments, the [1,2,3] triazole is a 1,4 disubstituted [1,2,3]-triazole. In some embodiments, the [1,2,3]-triazole is a 1,5-disubstituted [1,2,3]-triazole.

In some embodiments, the triazole is eluted by loading the column with an appropriate solvent or buffer solution and the solvent or buffer solution is passed through the column by gravity or centrifugation. In some embodiments, the triazole is eluted by loading the column with an appropriate solvent or buffer solution and the solvent or buffer solution is passed through the column by gravity. In some embodiments, wherein the triazole is eluted by loading the column with an appropriate solvent or buffer solution and the solvent or buffer solution is passed through the column by gravity, positive pressure from air or a compressed gas is also used to facilitate solvent or buffer solution flow. In some embodiments, the triazole is eluted by loading the column with an appropriate solvent or buffer solution and the solvent or buffer solution is passed through the column by centrifugation.

In some embodiments, the triazole is eluted by loading the centrifuge column with an appropriate buffer solution followed by centrifugation. In some embodiments, the trizole is eluted with an appropriate buffer solution followed by centrifuging the centrifuge column for a sufficient period of time.

In some embodiments, the triazole is a cell lysate derivatized product. In some embodiments, the cell lysate derivatized product is free or substantially free of impurities derived from cells and/or cell lysates. In some embodiments, the impurities include but are not limited to proteins and related materials derived from cells and/or cell lysates that are able to pass through the column matrix. In some embodiments, the cell lysate derivatized product requires secondary purification to remove trace impurities derived from cells and/or cell lysates. In some embodiments, the cell lysate derivatized product is free or substantially free of impurities derived from cell lysates. In some embodiments, the impurities include but are not limited to proteins and related materials derived from cell lysates that are able to pass through the column matrix. In some embodiments, the cell lysate derivatized product requires secondary purification to remove trace impurities derived from cell lysates. In some embodiments, secondary purification is any one of the methods disclosed herein for additional purification.

Provided herein is a method for preparing a glycosylated DNA from a reaction catalyzed by a heterogeneous copper catalyst, comprising mixing an alkynyl DNA component and an azido carbohydrate component in an appropriate solvent to form a solution; transferring the solution containing the alkynyl DNA component and the azido carbohydrate component to a column with a matrix barrier at the bottom of the column; wherein the column comprises a matrix of a copper (II) precatalyst and a reducing agent; wherein a copper (I) catalyst is generated from the reduction of the copper (II) precatalyst with the reducing agent; and passing the solution containing the alkynyl DNA component and the azido carbohydrate component; wherein upon contact with the copper (I) catalyst within the matrix, the alkynyl DNA component and the azido carbohydrate component react to form a glycosylated DNA.

Provided herein is a method for preparing a glycosylated DNA from a reaction catalyzed by a heterogeneous copper catalyst, comprising mixing an alkynyl DNA component and an azido carbohydrate component in an appropriate solvent to form a solution; transferring the solution containing the alkynyl DNA component and the azido carbohydrate component to a centrifuge column with a matrix barrier at the bottom of the column; wherein the centrifuge column comprises a matrix of a copper (II) precatalyst and a reducing agent; wherein a copper (I) catalyst is generated from the reduction of the copper (II) precatalyst with the reducing agent; and passing the solution containing the alkynyl DNA component and the azido carbohydrate component through the centrifuge column by centrifuging the centrifuge column for a sufficient period of time; wherein upon contact with the copper (I) catalyst within the matrix, the alkynyl DNA component and the azido carbohydrate component react to form a glycosylated DNA.

Azido carbohydrates contemplated for use include any carbohydrates that contain an azide moiety. In some embodiments, the azido carbohydrate contains cells and/or cell lysates. In some embodiments, the azido carbohydrate contains cell lysates. Alkynyl DNA contemplated for use include any DNA that contain an alkynyl moiety. In some embodiments, the alkynyl DNA contains cells and/or cell lysates. In some embodiments, the alkynyl DNA contains cell lysates.

The copper catalyzed cycloaddition or [3+2] of an alkynyl DNA with the azido carbohydrate forms a glycosylated DNA. In some embodiments, the glycosylated DNA is a [1,2,3]-triazole. In some embodiments, the [1,2,3] triazole is a 1,4 disubstituted [1,2,3]-triazole. In some embodiments, the [1,2,3]-triazole is a 1,5-disubstituted [1,2,3]-triazole.

Once the glycosylated DNA is formed, the glycosylated DNA is eluted by loading the centrifuge column with an appropriate buffer solution followed by centrifugation. In some embodiments, the glycosylated DNA is eluted with an appropriate buffer solution followed by centrifuging the centrifuge column for a sufficient period of time.

In some embodiments, the glycosylated DNA is a cell lysate derivatized product. In some embodiments, the cell lysate derivatized product is free or substantially free of impurities derived from cells and/or cell lysates. In some embodiments, the impurities include but are not limited to proteins and related materials derived from cells and/or cell lysates that are able to pass through the column matrix. In some embodiments, the cell lysate derivatized product requires secondary purification to remove trace impurities derived from cells and/or cell lysates. In some embodiments, the cell lysate derivatized product is free or substantially free of impurities derived from cell lysates. In some embodiments, the impurities include but are not limited to proteins and related materials derived from cell lysates that are able to pass through the column matrix. In some embodiments, the cell lysate derivatized product requires secondary purification to remove trace impurities derived from cell lysates. In some embodiments, secondary purification is any one of the methods disclosed herein for additional purification.

Provided herein is a method for preparing a fluorescent labeled peptide from a reaction catalyzed by a heterogeneous copper catalyst, comprising mixing an alkynyl peptide component and an azido fluorogenic dye component in an appropriate solvent to form a solution; transferring the solution containing the alkynyl peptide component and the azido fluorogenic dye component to a column with a matrix barrier at the bottom of the column; wherein the column comprises a matrix of copper (II) precatalyst and a reducing agent; wherein a copper (I) catalyst is generated from the reduction of the copper (II) precatalyst with the reducing agent; and passing the solution containing the alkynyl peptide component and the azido fluorogenic dye component through the column; wherein upon contact with the copper (I) catalyst within the matrix, the alkynyl peptide component and the azido fluorogenic component react to form a fluorescent labeled peptide.

Provided herein is a method for preparing a fluorescent labeled peptide from a reaction catalyzed by a heterogeneous copper catalyst, comprising mixing an alkynyl peptide component and an azido fluorogenic dye component in an appropriate solvent to form a solution; transferring the solution containing the alkynyl peptide component and the azido fluorogenic dye component to a centrifuge column with a matrix barrier at the bottom of the column; wherein the centrifuge column comprises a matrix of copper (II) precatalyst and a reducing agent; wherein a copper (I)

catalyst is generated from the reduction of the copper (II) precatalyst with the reducing agent; and passing the solution containing the alkynyl peptide component and the azido fluorogenic dye component through the centrifuge column by centrifuging the centrifuge column for a sufficient period of time; wherein upon contact with the copper (I) catalyst within the matrix, the alkynyl peptide component and the azido fluorogenic component react to form a fluorescent labeled peptide.

Azido fluorogenic dyes contemplated for use include any fluorogenic dye that contains an azide moiety. In some embodiments, the azido fluorogenic dye contains cells and/or cell lysates. In some embodiments, the azido fluorogenic dye contains cell lysates. Alkynyl peptides contemplated for use include any peptide that contains an alkynyl moiety. In some embodiments, the alkynyl peptide contains cells and/or cell lysates. In some embodiments, the alkynyl peptide contains cell lysates. The copper catalyzed cycloaddition or [3+2] of an alkynyl peptide with the azido fluorogenic dye forms a fluorescent labeled peptide. In some embodiments, the fluorescent label peptide is a [1,2,3]-triazole. In some embodiments, the [1,2,3] triazole is a 1,4 disubstituted [1,2,3]-triazole. In some embodiments, the [1,2,3]-triazole is a 1,5-disubstituted [1,2,3]-triazole.

Once the fluorescent labeled peptide is formed, the fluorescent labeled peptide is eluted by loading the centrifuge column with an appropriate buffer solution followed by centrifugation. In some embodiments, the fluorescent labeled peptide is eluted with an appropriate buffer solution followed by centrifuging the centrifuge column for a sufficient period of time.

In some embodiments, the fluorescent labeled peptide is a cell lysate derivatized product. In some embodiments, the cell lysate derivatized product is free or substantially free of impurities derived from cells and/or cell lysates. In some embodiments, the impurities include but are not limited to proteins and related materials derived from cells and/or cell lysates that are able to pass through the column matrix. In some embodiments, the cell lysate derivatized product requires secondary purification to remove trace impurities derived from cells and/or cell lysates. In some embodiments, the cell lysate derivatized product is free or substantially free of impurities derived from cell lysates. In some embodiments, the impurities include but are not limited to proteins and related materials derived from cell lysates that are able to pass through the column matrix. In some embodiments, the cell lysate derivatized product requires secondary purification to remove trace impurities derived from cell lysates. In some embodiments, secondary purification is any one of the methods disclosed herein for additional purification.

A column matrix is used herein to immobilize the heterogeneous metal catalyst. Any type of solid support capable of immobilizing the heterogeneous metal catalyst is suitable for use as the column matrix. Suitable column matrices include but are not limited to, resins or supports that are polystyrene-based, polysaccharide based, polyamide-based, carbon-based, alumina-based, and silica-based. Further examples also include resins that are used for ion-exchange chromatography, affinity chromatography and size exclusion chromatography.

In some embodiments, the column matrix comprises a heterogeneous metal catalyst. In some embodiments, the column matrix is suitable for catalyzing the azide-alkyne cycloaddition. In some embodiments, the column matrix comprises a heterogeneous metal catalyst that catalyzes the azide-alkyne cycloaddition. In some embodiments, the heterogeneous metal catalyst comprises a copper catalyst, a ruthenium catalyst, a silver catalyst, or a zinc catalyst. In some embodiments, the heterogeneous metal catalyst comprises a copper catalyst. In some embodiments, the heterogeneous metal catalyst comprises a ruthenium catalyst. In some embodiments, the heterogeneous metal catalyst comprises a silver catalyst. In some embodiments, the heterogeneous metal catalyst comprises a zinc catalyst.

In some embodiments, the column matrix further comprises a resin or support that is polystyrene-based, polysaccharide based, polyamide-based, carbon-based, alumina-based, silica-based, or any combination thereof. In some embodiments, the column matrix further comprises a resin or support that is suitable for ion-exchange chromatography, affinity chromatography, or size exclusion chromatography. In some embodiments, the column matrix further comprises an ion-exchange resin, an affinity resin, a size-exclusion or any combination thereof.

In some embodiments, the column matrix further comprises an ion-exchange resin. In some embodiments, ion-exchange resin is anion exchange resin. Examples of anion exchange resins include strong anion resins, such as those containing quaternary ammonium groups, or weak anion exchange resins, such as those containing ammonium chloride or hydroxide groups.

In some embodiments, the ion-exchange resin is a cation exchange resin. Examples of cation exchange resins include strong cation exchange resins, such as those containing sulfonic acid groups or corresponding salts, and weak cation exchange resins, such as those containing carboxylic acid groups or the corresponding salts.

Examples of suitable ion-change resins include polystyrene-based resins, such as Amberlite®, Amberlyst®, Dowex®, Merrifield's peptide resin; polysaccharide-based resins, such as Sephadex®; polyethylenimine-based resins; and polyamide-based resins.

In some embodiments, the ion-exchange resin is polystyrene-based. In some embodiments, ion-exchange resin is polysaccharide-based. In some embodiments, the ion-exchange resin is polyethylenimine-based. In some embodiments, the ion-exchange resin is polyamide-based.

In some embodiments, the ion-exchange resin comprises polysaccharides that have been chemically modified. In some embodiments, the ion-exchange resin comprises polysaccharides modified with carboxymethyl functional groups, such as CM-cellulose. In some embodiments, the ion-exchange resin comprises polysaccharides with diethylaminoethyl groups, such as DEAE-cellulose.

In some embodiments, the column matrix further comprises an additional column matrix. In some embodiments, the additional column matrix comprises any type of solid support suitable for further purification. Suitable additional column matrices include but are not limited to, resins or supports that are polystyrene-based, polysaccharide based, polyamide-based, carbon-based, alumina-based, and silica-based. In some embodiments, the additional column matrix comprises a resin or support that is polystyrene-based, polysaccharide-based, polyamide-based, carbon-based, alumina-based, silica-based, or any combination thereof. In some embodiments, the additional column matrix comprises a resin or support that is polystyrene based. In some embodiments, the additional column matrix comprises a resin or support that is polysaccharide based. In some embodiments, the additional column matrix comprises a resin or support that is polyamide-based. In some embodiments, the additional column matrix comprises a resin or support that is carbon-based. In some embodiments, the additional column matrix comprises a resin or support that is alumina-based. In some embodiments, the additional column matrix comprises a resin or support that is silica based.

Further examples also include resins that are used for ion-exchange chromatography, affinity chromatography, and size-exclusion chromatography. In some embodiments, the additional column matrix comprises an ion-exchange resin, an affinity resin, a size-exclusion or any combination thereof. In some embodiments, the additional column matrix comprises a size-exclusion resin. In some embodiments, the additional column matrix comprises an ion-exchange resin. In some embodiments, the additional column matrix comprises an affinity resin. Transition Metal Catalysts In some embodiments, the column matrix comprises a heterogeneous metal catalyst. In some embodiments, the heterogeneous metal catalyst is a catalyst suitable for catalyzing the azide-alkyne cycloaddition. Examples such heterogeneous metal catalysts include but are not limited to copper catalysts, ruthenium catalysts, silver catalysts and zinc catalysts. In some embodiments, the heterogeneous metal catalyst comprises a copper catalyst, a ruthenium catalyst, a silver catalyst, or a zinc catalyst. In some embodiments, the heterogeneous metal catalyst comprises a copper catalyst. In some embodiments, the heterogeneous metal catalyst comprises a ruthenium catalyst. In some embodiments, the heterogeneous metal catalyst comprises a silver catalyst. In some embodiments, the heterogeneous metal catalyst comprises a zinc catalyst.

In some embodiments, the heterogeneous metal catalyst further comprises a heterogeneous metal precatalyst and reducing agent, wherein reduction of the precatalyst by the reducing agent generates the catalytically active species. In some embodiments, the heterogeneous metal catalyst further comprises a heterogeneous precatalyst and an oxidizing agent, wherein the oxidation of the precatalyst by the oxidizing agent generates the catalytically active species.

In some embodiments, the column matrix comprises a heterogeneous ruthenium catalyst. In some embodiments, the heterogeneous ruthenium catalyst comprises a ruthenium (II) catalyst. In some embodiments, the ruthenium catalyst (II) further comprises a pentamethylcyclopentadienyl (Cp*) ligand. In some embodiments, the ruthenium catalyst (II) further comprises a cyclopentadienyl (Cp) ligand. In some embodiments, the ruthenium catalyst comprises a pentamethylcyclopentadienyl ruthenium chloride [Cp*RuCl] complex. In some embodiments, the ruthenium catalyst is pentamethylcyclopentadienylbis(triphenylphosphine)ruthenium (II) chloride (Cp*RuCl(PPh$_3$)$_2$). In some embodiments, the ruthenium catalyst is chloro(1,5-cyclooctadiene)(pentamethylcyclopentadienyl)ruthenium (Cp*RuCl(COD), COD=1,5-cyclooctadiene).

In some embodiments, the column matrix comprises a heterogeneous silver catalyst. In some embodiments, the heterogeneous silver catalyst comprises a silver (I) catalyst. In some embodiments, the column matrix comprises a heterogeneous zinc catalyst.
Heterogeneous Copper Catalyst In some embodiments, the column matrix comprises a heterogeneous copper catalyst. In some embodiments, the heterogeneous copper catalyst comprises a copper(II) precatalyst and a reducing agent, wherein the reducing agent reduces the copper(II) precatalyst to form the active copper (I) catalyst required for the azide-alkyne cycloaddition. In some embodiments, the heterogeneous copper catalyst comprises a copper (I) catalyst. In some embodiments, the heterogeneous copper catalyst comprises a copper(0) precatalyst and an oxidizing agent, wherein the oxidizing agent oxidizes the copper(0) precatalyst to form the active copper (I) catalyst required for the azide-alkyne cycloaddition.

Copper (0) precatalysts contemplated for use include any copper (0) sources are capable of being oxidized to copper (I) by an oxidizing agent to catalyzing the azide-alkyne cycloaddition reaction. Examples of such copper (0) precatalyst include but are not limited to copper metal, copper wire, copper turnings, copper powder and copper nanoparticles. An example of suitable oxidizing agent includes but is not limited to copper sulfate.

Copper (I) catalysts contemplated for use include any copper (I) salts or copper (I)-ligand that are capable of catalyzing the azide-alkyne cycloaddition reaction. Examples of such copper (I) salts that are suitable include, but are not limited, to copper(I) bromide, copper (I) iodide, and copper (I) tetrakis(acetonitrile) hexafluorophosphate. Examples of copper (I)-ligand complexes that are suitable include but not limited to any copper (I)-ligand complexes wherein the ligand is any one of the ligands described in this application.

Copper (II) precatalysts contemplated for use include any copper (II) salts or copper (II)-ligand complexes that are reduced to form the catalytically active copper(I) species required for the copper catalyzed azide-alkyne cycloaddition reaction. Examples of such copper (II) salts that are suitable as copper (II) precatalysts include, but are not limited, to copper(II) acetate, copper (II) chloride, copper (II) bromide, copper(II) trifluoromethanesulfonate, and copper (II) sulfate. Examples of copper (II)-ligand complexes that are suitable copper (II) precatalysts include but not limited, to any of the copper (II)-ligand complexes wherein the ligand is any of the ligands described in this application.

In some embodiments, the copper (II) precatalyst is [Cu(1,10-phenanthroline-5,6-dione)$_2$]$^{2+}$. In some embodiments, the copper (II) precatalyst is [Cu(4,7-diphenyl-1,10-phenanthroline-disulfonic acid)$_2$]$^{2-}$.

In some embodiments, a ligand is employed to stabilize the active copper (I) catalyst. In some embodiments, the copper (II) precatalyst further comprises a ligand.

Examples of suitable ligands include, but are not limited to, substituted tris(triazolyl)methylamines and tris(benzimidazolylmethyl)amines. Examples of tris(triazolylmethyl) amines and tris(benzimidazolylmethyl)amines include, but are not limited to, tris[(1-benzyl-1H-1,2,3-triazol-4-yl) methyl]amine (TBTA); tris(3-hydroxypropyltriazolylmethyl)amine (THPTA); tris(2-benzimidazolylmethyl)amine (BimH)$_3$; and tripotassium 5,5',5''-[2,2',2''-nitrilotris(methylene)tris(1H-benzimidazole-2,1-diyl)]tripentanoate hydrate (BimC4A)$_3$.

Examples of other ligands contemplated for use further include, but are not limited to, bipyridines, phenanthrolines, pyridine bis(oxazoline) (PyBOX) and derivatives thereof. Examples of bipyridines and phenanthrolines include but are not limited to 2,2'-bipyridine, 4-4'-dimethoxy-2-2'-bipyridine, 4,4'-dimethyl-2,2'-bipyridine, 2,6-bis(2-pyridyl)pyridine (terpyridine),1,10-phenanthroline, bathophenanthroline, and 4,7-diphenyl-1,10-phenanthrolinedisulfonic acid (4,7-diphenyl-1,10-phenanthroline disulfonic acid disodium salt hydrate).

In some embodiments, the ligand is phenanthroline derivative. In some embodiments, the ligand is 1,10-phenanthroline. In some embodiments, the ligand is 4,7-diphenyl-1,10-phenanthrolinedisulfonic acid.

Reducing agents contemplated for use include any reducing agent capable of reducing the copper (II) precatalyst to form the catalytically active copper (I) species required for the copper catalyzed azide-alkyne cycloaddition. Suitable reducing agents include metallic based reducing agents, such as Cu, Al, Be, Co, Cr, Fe, Mg, Mn, Ni and Zn. A particular example of a suitable reducing agent is zinc amalgam. Other reducing agents, include but are not limited to, ascorbate, quinone, hydroquinone, vitamin $K_1$, glutathione, and cysteine.

In some embodiments, the reducing agent is a metallic based reducing agent. In some embodiments, the reducing agent is zinc amalgam.

In some embodiments, further purification is achieved by incorporating an additional matrix to the centrifuge column such that once the triazole product has been formed in matrix comprising that heterogeneous copper catalyst, the product is eluted through the additional matrix. In some embodiments, the additional matrix is a resin that is suitable for the purification of the triazole product. In some embodiments, the additional matrix comprises a resin or support that is polystyrene-based, polysaccharide-based, polyamide-based, carbon-based, alumina-based, silica-based, or any combination thereof. In some embodiments, the additional matrix comprises an ion-exchange resin, an affinity resin, a size-exclusion or any combination thereof. In some embodiments the additional matrix is a size-exclusion resin.

In some embodiments, further purification is achieved by incorporating a size-exclusion resin to the centrifuge column such that once the triazole product has been formed in matrix comprising that heterogeneous copper catalyst, the product is eluted through a layer of size-exclusion resin. In some embodiments, the centrifuge column further comprises a size-exclusion resin. Size-exclusion resins suitable for use include those that are polystyrene-based, polysaccharide-based, or polyamide-based. In some embodiments, the size-exclusion resin is polystyrene-based, polysaccharide-based, polyamide-based, or any combination thereof. In some embodiments, the size-exclusion resin is polystyrene-based. In some embodiments, the size-exclusion resin is polysaccharide-based. In other embodiments, the size-exclusion resin is polyamide based.

Column Matrix

Provided herein is a column matrix comprising a heterogeneous metal catalyst. Also provided herein is a column matrix comprising a heterogeneous metal catalyst that catalysts the azide-alkyne cycloaddition. In some embodiments, the heterogeneous metal catalyst comprises a copper catalyst, a ruthenium catalyst, a silver catalyst, or a zinc catalyst. In some embodiments, the column matrix comprises a copper catalyst. In some embodiments, the column matrix comprises a ruthenium catalyst. In some embodiments, the column matrix comprises a silver catalyst. In some embodiments, the column matrix comprises a zinc catalyst. In some embodiments, the heterogeneous metal catalyst further comprises a ligand. In some embodiments, the column matrix comprises a heterogeneous metal precatalyst and reducing agent. In some embodiments, the column matrix comprises a heterogeneous metal precatalyst and oxidizing agent.

In some embodiments, the copper catalyst further comprises a ligand. In some embodiments, the copper catalyst comprises a copper (I) catalyst. In some embodiments, the copper catalyst comprises a copper (II) precatalyst and a reducing agent. In some embodiments, the copper (II) precatalyst further comprises a ligand. In some embodiments, the reducing agent is zinc amalgam. In some embodiments, the copper catalyst comprises a copper (0) precatalyst and an oxidizing agent.

In some embodiments, the copper catalyst comprises a copper (II) precatalyst and a reducing agent, wherein the reducing agent reduces the copper(II) precatalyst to form the active copper (I) catalyst required for the azide-alkyne cycloaddition. In some embodiments, the copper catalyst comprises a copper (I) catalyst. In some embodiments, the copper catalyst comprises a copper(0) precatalyst and an oxidizing agent, wherein the oxidizing agent oxidizes the copper(0) precatalyst to form the active copper (I) catalyst required for the azide-alkyne cycloaddition.

In some embodiments, the ruthenium catalyst further comprises a ligand. In some embodiments, the ruthenium catalyst comprises a ruthenium (II) catalyst.

Provided herein is a column matrix comprising a heterogeneous copper catalyst. Also provided herein is a column matrix comprising a heterogeneous copper catalyst that catalysts the azide-alkyne cycloaddition.

In some embodiments, the heterogeneous copper catalyst further comprises a ligand. In some embodiments, the heterogeneous copper catalyst comprises a copper (I) catalyst. In some embodiments, the heterogeneous copper catalyst comprises a copper (II) precatalyst and a reducing agent. In some embodiments, the copper (II) precatalyst further comprises a ligand. In some embodiments, the reducing agent is zinc amalgam. In some embodiments, the heterogeneous copper catalyst comprises a copper (0) precatalyst and an oxidizing agent.

In some embodiments, the heterogeneous copper catalyst comprises a copper (II) precatalyst and a reducing agent, wherein the reducing agent reduces the copper(II) precatalyst to form the active copper (I) catalyst required for the azide-alkyne cycloaddition. In some embodiments, the heterogeneous copper catalyst comprises a copper (I) catalyst. In some embodiments, the heterogeneous copper catalyst comprises a copper(0) precatalyst and an oxidizing agent, wherein the oxidizing agent oxidizes the copper(0) precatalyst to form the active copper (I) catalyst required for the azide-alkyne cycloaddition.

Provided herein is a column matrix comprising a copper (I) catalyst. Also provided herein is a column matrix comprising a copper (II) catalyst and a reducing agent. In some embodiments, the reducing agent is zinc amalgam. Further provided herein is a column matrix comprising a copper (II) catalyst and zinc amalgam.

Provided herein is a column matrix for use in bioconjugation comprising a copper (I) catalyst. Also provided herein is a column matrix for use in bioconjugation comprising a copper (II) precatalyst and a reducing agent. In some embodiments, the reducing agent is zinc amalgam. Further provided herein is a column matrix for use in bioconjugation comprising a copper (II) precatalyst and zinc amalgam.

Provided herein is a column matrix for use in bioconjugation catalyzed by a heterogeneous copper catalyst comprising a copper (I) catalyst. Also provided herein is a column matrix for use in bioconjugation catalyzed by a heterogeneous copper comprising a copper (II) precatalyst and a reducing agent. In some embodiments, the reducing agent is zinc amalgam. Further provided herein is a column matrix for use in bioconjugation catalyzed by a heterogeneous copper comprising a copper (II) precatalyst and zinc amalgam. In some embodiments, the copper (II) precatalyst further comprises a ligand.

In some embodiments, the column matrix further comprises a resin or support that is polystyrene-based, polysaccharide based, polyamide-based, carbon-based, alumina-based, silica-based, or any combination thereof. In some embodiments, the column matrix further comprises a resin or support that is suitable for ion-exchange chromatography, affinity chromatography, or size exclusion chromatography.

In some embodiments, the column matrix further comprises an ion-exchange resin, an affinity resin, a size-exclusion or any combination thereof.

In some embodiments, the column matrix further comprises an ion-exchange resin. In some embodiments, the ion-exchange resin is an anion exchange resin or a cation exchange resin. In some embodiments, the column matrix further comprises a size-exclusion resin.

In some embodiments, the column matrix is suitable for use in gravity column chromatography, or in centrifugal column chromatography. In some embodiments, the column matrix is suitable use in gravity column chromatography. In some embodiments, the column matrix is suitable for use in centrifugal column chromatography. In some embodiments, the centrifugal column chromatography is microspin column chromatography. In some embodiments, column matrix is suitable for use in microspin column chromatography. In some embodiments, the column matrix is suitable for use in azide-alkyne cycloaddition.

In some embodiments, the column matrix further comprises an additional matrix. In certain embodiments, the additional matrix is a resin suitable for the purification of a cycloaddition compound formed from the azide-alkyne cycloaddition (e.g., a triazole). In certain embodiments, the additional matrix is a resin suitable for the purification of a product. In certain embodiments, the product is a triazole formed from a heterogeneous metal-catalyzed azide alkyne cycloaddition. In some embodiments, the column matrix further comprises an additional matrix that is a resin suitable for the purification of a cycloaddition compound formed from the azide-alkyne cycloaddition. In certain embodiments, the additional matrix is a size-exclusion resin.

The column matrix comprising the heterogeneous metal catalyst is prepared through a variety of methods. In some embodiments, the column matrix is prepared by mixing the metal catalyst with the appropriate resin or solid support. In some embodiments, the column matrix is prepared by adding the metal catalyst to a mixture comprising at least one appropriate resin or solid support. In some embodiments, when heterogeneous metal precatalysts are used, the column matrix is prepared by pre-mixing the metal precatalyst and resin or resins in an appropriate buffer solution or solvent to form a suspension and then adding the appropriate reducing agent or oxidizing agent to the suspension. The reducing agent or oxidizing agent is then mixed into the suspension.

In some embodiments, the resin premixed with the metal catalyst is polystyrene-based, polysaccharide-based, polyamide-based, carbon-based, alumina-based, silica-based, or any combination thereof. In some embodiments, the resin premixed with the metal catalyst is polystyrene-based. In some embodiments, the resin premixed with the metal catalyst is polysaccharide-based. In some embodiments, the resin premixed with the metal catalyst is polyamide-based. In some embodiments, the resin premixed with the metal catalyst is carbon-based. In some embodiments, the resin premixed with the metal catalyst is alumina-based. In some embodiments, the resin premixed with the metal catalyst is silica-based.

In some embodiments, the resin premixed with the metal catalyst is an ion-exchange resin, affinity resin, size-exclusion resin, or a combination thereof. In some embodiments, the resin premixed with the metal catalyst is an affinity resin. In some embodiments, the resin premixed with the metal catalyst is a size-exclusion resin. In some embodiments, the resin premixed with the metal catalyst is an ion-exchange. In other embodiments, the ion-exchange resin is a cation exchange resin. The type of ion-exchange resin used would depend on the overall charge of the alkyne and/or azide components used. For instance, if an alkynyl DNA is used, then a cation exchange resin is used. If an alkynyl peptide is positively charged, then an anion exchange column is used.

In some embodiments, the resin is premixed with a metal catalyst that catalyzes the azide-alkynyl cycloaddition. In some embodiments, the resin is premixed with a copper catalyst. In some embodiments, the resin is premixed with a ruthenium catalyst. In some embodiments, the resin is premixed with a silver catalyst. In some embodiments, the resin is premixed with a zinc catalyst. In some embodiments, the resin is premixed with a metal precatalyst and reducing agent. In some embodiments, the resin is premixed a metal precatalyst and an oxidizing agent.

The column matrix comprising the heterogeneous copper catalyst is prepared similarly. In some embodiments, the column matrix is prepared by mixing the copper catalyst with the appropriate resin or solid support. In some embodiments, the column matrix is prepared by mixing the copper catalyst to a mixture comprising at least one the appropriate resin or solid support. In some embodiments, the column matrix is prepared by pre-mixing the copper (II) precatalyst and resin in an appropriate buffer to form a suspension and then adding the reducing agent to the suspension. The reducing agent is then mixed into the suspension. In some embodiments, the reducing agent added is zinc amalgam. The column matrix will turn into an intense olive green, indicating that the catalytically active copper (I) catalyst has been formed. The column matrix is then ready for use and is transferred to the centrifuge column. In some embodiments, the reducing agent is pre-mixed with the resin or resins and the copper (II) precatalyst is added to the pre-mixture. In some embodiments, a copper (I) catalyst is added to the resin instead of a copper (II) precatalyst and a reducing agent. In some embodiments, a copper (0) precatalyst and oxidizing agent is used instead of a copper (II) precatalyst and a reducing agent.

In some embodiments, the resin premixed with the copper catalyst is polystyrene-based, polysaccharide-based, polyamide-based, carbon-based, alumina-based, silica-based, or any combination thereof. In some embodiments, the resin premixed with the copper catalyst is polystyrene-based. In some embodiments, the resin premixed with the copper catalyst is polysaccharide-based. In some embodiments, the resin premixed with the copper catalyst is polyamide-based. In some embodiments, the resin premixed with the copper catalyst is carbon-based. In some embodiments, the resin premixed with the copper catalyst is alumina-based. In some embodiments, the resin premixed with the copper catalyst is silica-based.

In some embodiments, the resin premixed with the copper catalyst is an ion-exchange resin, affinity resin, size-exclusion resin, or a combination thereof. In some embodiments, the resin premixed with the copper catalyst is an affinity resin. In some embodiments, the resin premixed with the copper catalyst is a size-exclusion resin. In some embodiments, the resin premixed with the copper catalyst is an ion-exchange. In other embodiments, the ion-exchange resin is a cation exchange resin.

The type of ion-exchange resin used depends on the overall charge of the alkyne and/or azide components used. For instance, if an alkynyl DNA is used, then a cation exchange resin is used. If an alkynyl peptide is positively charged, then an anion exchange column is used.

Furthermore, the type of cation-exchange resin used also correlates to the type of copper (II) precatalyst used. In some embodiments, when a cation-exchange resin is used, then the copper (II) precatalyst is [Cu(1,10-phenanthroline-5,6-dione)$_2$]$^{2+}$. In some embodiments, when an anion-exchange resin is used, then the copper (II) precatalyst is [Cu(4,7-diphenyl-1,10-phenanthroline-disulfonic acid)2]$^{2-}$.

Column

Provided herein is a column comprising a matrix of a heterogeneous metal catalyst. In some embodiments, the heterogeneous metal catalyst comprises a metal catalyst suitable for catalyzing the azide-alkyne cycloaddition. Also provided herein is a column comprising a matrix of a heterogeneous metal catalyst that catalyzes the azide-alkyne cycloaddition. In some embodiments, the heterogeneous metal catalyst comprises a copper catalyst, a ruthenium catalyst, a silver catalyst, or zinc catalyst. In some embodiments, the heterogeneous metal catalyst comprises a copper catalyst. In some embodiments, the heterogeneous metal catalyst comprises a ruthenium catalyst. In some embodiments, the heterogeneous metal catalyst comprises a silver catalyst. In some embodiments, the heterogeneous metal catalyst comprises a zinc catalyst. In some embodiments, the heterogeneous metal catalyst further comprises a ligand. In some embodiments, the heterogeneous metal catalyst further comprises a heterogeneous metal precatalyst and reducing agent. In some embodiments, the heterogeneous metal catalyst further comprises a heterogeneous metal precatalyst and oxidizing agent.

In some embodiments, the copper catalyst further comprises a ligand. In some embodiments, the copper catalyst comprises a copper (I) catalyst. In some embodiments, the copper catalyst comprises a copper (II) precatalyst and a reducing agent. In some embodiments, the copper (II) precatalyst further comprises a ligand. In some embodiments, the reducing agent is zinc amalgam. In some embodiments, the copper catalyst comprises a copper (0) precatalyst and an oxidizing agent.

In some embodiments, the copper catalyst comprises a copper (II) precatalyst and a reducing agent, wherein the reducing agent reduces the copper (II) precatalyst to form the active copper (I) catalyst required for the azide-alkyne cycloaddition. In some embodiments, the copper catalyst comprises a copper (I) catalyst. In some embodiments, the copper catalyst comprises a copper (0) precatalyst and an oxidizing agent, wherein the oxidizing agent oxidizes the copper (0) precatalyst to form the active copper (I) catalyst required for the azide-alkyne cycloaddition.

In some embodiments, the ruthenium catalyst further comprises a ligand. In some embodiments, the ruthenium catalyst comprises a ruthenium (II) catalyst.

Provided herein is a column comprising a matrix of a heterogeneous copper catalyst. Also provided herein is a column comprising a matrix of a heterogeneous copper catalyst that catalyzes the azide-alkyne cycloaddition.

In some embodiments, the heterogeneous copper catalyst further comprises a ligand. In some embodiments, the heterogeneous copper catalyst comprises a copper (I) catalyst. In some embodiments, the heterogeneous copper catalyst comprises a copper (II) precatalyst and a reducing agent. In some embodiments, the heterogeneous copper (II) precatalyst further comprises a ligand. In some embodiments, the reducing agent is zinc amalgam. In some embodiments, the heterogeneous copper catalyst comprises a copper (0) precatalyst and an oxidizing agent.

Provided herein is a column comprising a matrix of a copper (I) catalyst. Also provided herein is a column comprising a matrix of a copper (II) precatalyst and a reducing agent. In some embodiments, the reducing agent is zinc amalgam. Further provided is a column comprising a matrix of a copper (II) precatalyst and zinc amalgam.

Provided herein is a column for use in bioconjugation comprising a matrix of a copper (I) catalyst. Also provided herein is a column for use in bioconjugation comprising a matrix of a copper (II) precatalyst and a reducing agent. In some embodiments, the reducing agent is zinc amalgam. Further provided is a column for use in bioconjugation comprising a matrix of a copper (II) precatalyst and zinc amalgam.

Provided herein is a column for use in bioconjugation catalyzed by a heterogeneous copper catalyst comprising a matrix of a copper (I) catalyst. Also provided herein is a column for use in bioconjugation catalyzed by a heterogeneous copper catalyst comprising a matrix of a copper (II) precatalyst and a reducing agent. In some embodiments, the reducing agent is zinc amalgam. Further provided is a column for use in bioconjugation catalyzed by a heterogeneous copper catalyst comprising a matrix of a copper (II) precatalyst and zinc amalgam.

In some embodiments, the column is a gravity column or a centrifuge column. In some embodiments, the column is a gravity column. In some embodiments, the column is a centrifuge column. In some embodiments, the centrifuge column is suitable for use in microspin column chromatography.

A schematic showing an embodiment of the column is shown in FIG. 1. As used herein, a column is meant to encompass any column that is suitable for any sample size and volume as long as the column allows for chromatographic separation. As shown in FIG. 1, the matrix comprising the heterogeneous metal catalyst is loaded into the column. Furthermore, in some embodiments the column comprises an additional column matrix to allow for further purification.

In some embodiments, the column further comprises an additional column matrix. In some embodiments, the column further comprises at least one additional column matrix. In some embodiments, the additional column matrix is a resin suitable for the purification of a cycloaddition compound formed from the azide-alkyne cycloaddition. In certain embodiments, the additional column matrix is a resin suitable for the purification of a product. In certain embodiments, the product is a triazole formed from a heterogeneous metal-catalyzed azide alkyne cycloaddition.

In some embodiments, the column further comprises an additional column matrix that is a resin suitable for the purification of a cycloaddition compound formed from the azide-alkyne cycloaddition.

Such additional columns matrices are resins that include and are not limited to affinity column resins, ion-exchange resins, or size-exclusion resins. In some embodiments, additional column matrix is an affinity resin, an ion-exchange resin, or size-exclusion resin. In some embodiments, the column further comprises an affinity column resin, an ion-exchange resin, a size-exclusion resin or any combination thereof.

In some embodiments, the additional column matrix is polystyrene-based, polysaccharide-based, polyamide-based, carbon-based, alumina-based, silica-based, or any combination thereof. In some embodiments, the additional column matrix is polystyrene-based. In some embodiments, the additional column matrix is polysaccharide-based. In some embodiments, the additional column matrix is polyamide-based. In some embodiments, the additional column matrix is carbon-based. In some embodiments, the additional column matrix is alumina-based. In some embodiments, the additional column matrix is silica-based.

Although FIG. 1 shows a column comprising of at least one additional column matrix, there are embodiments wherein a column has two, three, four, or more additional column matrices. In some embodiments, the additional column matrix or matrices precede the matrix comprising the heterogeneous metal complex catalysts. In some embodiments, the additional column matrices precede and follow the matrix comprising the heterogeneous catalyst.

Furthermore, although FIG. 1 is a schematic for an embodiment of a centrifuge column, that configuration of the column shown in FIG. 1 is non-limiting. The columns contemplated for use are any columns capable of chromatographic separation for any sample size and volume. Such columns include columns wherein the solvent or buffer solution is passed through the column matrix by gravity or centrifugal force. In some embodiments, wherein the solvent or buffer solution is passed through the column matrix through gravity, positive pressure from air or compressed gas is also used to facilitate solvent flow. Examples of suitable compressed gas include compressed air, nitrogen, and argon.

In some embodiments, the column is suitable for use in gravity chromatography and centrifugal chromatography. In some embodiments, the column is suitable for gravity chromatography. In some embodiments, the column is suitable for use in centrifugal chromatography.

Provided herein is a gravity column comprising a matrix of a copper (I) catalyst. Also provided herein is a gravity column comprising a matrix of a copper (II) precatalyst and a reducing agent. In some embodiments, the reducing agent is zinc amalgam. Further provided is a gravity column comprising a matrix of a copper (II) precatalyst and zinc amalgam.

Provided herein is a gravity column for use in bioconjugation comprising a matrix of a copper (I) catalyst. Also provided herein is a gravity column for use in bioconjugation comprising a matrix of a copper (II) precatalyst and a reducing agent. In some embodiments, the reducing agent is zinc amalgam. Further provided is a gravity column for use in bioconjugation comprising a matrix of a copper (II) precatalyst and zinc amalgam.

Provided herein is a gravity column for use in bioconjugation catalyzed by a heterogeneous copper catalyst comprising a matrix of a copper (I) catalyst. Also provided herein is a gravity column for use in bioconjugation catalyzed by a heterogeneous copper catalyst comprising a matrix of a copper (II) precatalyst and a reducing agent. In some embodiments, the reducing agent is zinc amalgam. Further provided is a gravity column for use in bioconjugation catalyzed by a heterogeneous copper catalyst comprising a matrix of a copper (II) precatalyst and zinc amalgam.

Provided herein is a centrifuge column comprising a matrix of a copper (I) catalyst. Also provided herein is a centrifuge column comprising a matrix of a copper (II) precatalyst and a reducing agent. In some embodiments, the reducing agent is zinc amalgam. Further provided is a centrifuge column comprising a matrix of a copper (II) precatalyst and zinc amalgam.

Provided herein is a centrifuge column for use in bioconjugation comprising a matrix of a copper (I) catalyst. Also provided herein is a centrifuge column for use in bioconjugation comprising a matrix of a copper (II) precatalyst and a reducing agent. In some embodiments, the reducing agent is zinc amalgam. Further provided is a centrifuge column for use in bioconjugation comprising a matrix of a copper (II) precatalyst and zinc amalgam.

Provided herein is a centrifuge column for use in bioconjugation catalyzed by a heterogeneous copper catalyst comprising a matrix of a copper (I) catalyst. Also provided herein is a centrifuge column for use in bioconjugation catalyzed by a heterogeneous copper catalyst comprising a matrix of a copper (II) precatalyst and a reducing agent. In some embodiments, the reducing agent is zinc amalgam. Further provided is a centrifuge column for use in bioconjugation catalyzed by a heterogeneous copper catalyst comprising a matrix of a copper (II) precatalyst and zinc amalgam.

In some embodiments, the matrix further comprises an ion-exchange resin. In some embodiments, the ion-exchange resin is an anion exchange resin or a cation exchange resin. In some embodiments, the matrix further comprises a size-exclusion resin. In some embodiments, the copper (II) precatalyst further comprises a ligand. In some embodiments, the centrifuge column is suitable for use in azide-alkyne cycloaddition.

Figure 2:
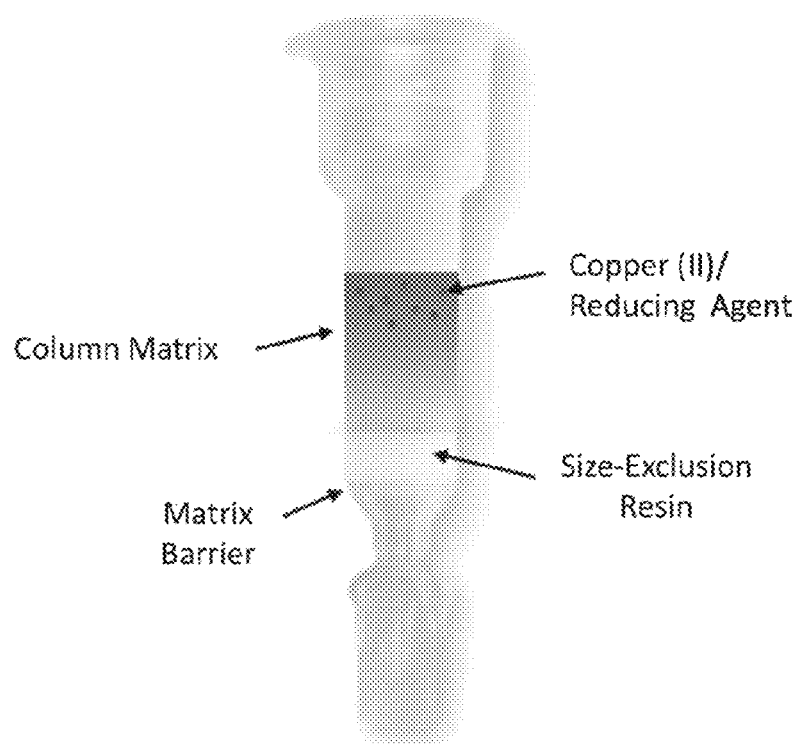
FIG. 2 depicts a schematic diagram of a particular embodiment of the centrifuge column, wherein the centrifuge column comprises a matrix containing a heterogeneous copper catalyst (II) precatalyst and reducing agent, and the centrifuge column further comprises a size-exclusion resin.

A schematic showing an embodiment of the centrifuge column is shown in FIG. 2. As used herein, a centrifuge column is meant to encompass any column that is suitable for any sample size and volume as long as the column allows for centrifugation. In some embodiments, the centrifuge column is suitable for use in microspin column chromatography. As shown in FIG. 2, the matrix comprising the heterogeneous copper catalyst is loaded in to the centrifuge column. Furthermore, in some embodiments the centrifuge column comprises an additional column matrix to allow for further purification. The additional column matrix shown in FIG. 2 is a size-exclusion resin.

In some embodiments, the centrifuge column further comprises at least one additional column matrix. In certain embodiments, the additional column matrix is a resin suitable for the purification of a product. In certain embodiments, the product is a triazole formed from a heterogeneous metal-catalyzed azide alkyne cycloaddition.

Such additional columns matrices are resins that include and are not limited to affinity column resins, ion-exchange resins, or size-exclusion resins. In some embodiments, additional column matrix is an affinity resin, an ion-exchange resin, or size-exclusion resin. In some embodiments, the centrifuge column further comprises an affinity column resin, an ion-exchange resin, a size-exclusion resin or any combination thereof In some embodiments, the additional column matrix is polystyrene-based, polysaccharide-based, polyamide-based, carbon-based, alumina-based, silica-based, or any combination thereof. In some embodiments, the additional column matrix is polystyrene-based. In some embodiments, the additional column matrix is polysaccharide-based. In some embodiments, the additional column matrix is polyamide-based. In some embodiments, the additional column matrix is carbon-based. In some embodiments, the additional column matrix is alumina-based. In some embodiments, the additional column matrix is silica-based.

Although FIG. 2 shows a centrifuge column comprising of at least one additional column matrix, there are embodiments wherein a centrifuge column has two, three, four, or more additional column matrices.

Furthermore, although FIG. 2 is a schematic for an embodiment of a centrifuge column, that configuration of the column shown in FIG. 2 is non-limiting.

EXAMPLES

The present invention may be better understood through reference to the following examples. These examples are included to describe exemplary embodiments only and should not be interpreted to encompass the entire breadth of the invention.

Example 1

Preparation of Zinc Amalgam 3 g of zinc granules (~1 mm diameter) were placed in a 500 mL Erlenmeyer flask. The granules were washed with 2 mL of 6 M HCl for 5 seconds and then washed 8 times with 10 mL aliquots of water. After the final wash, 15 mL of 0.25 M $HgCl_2$ were added, and the flask was left to sit for 5 minutes. The liquid was then poured off, and the zinc amalgam was washed with 10 mL aliquots of water 8 more times.

Example 2

Preparation of Centrifuge Column with Matrix Comprising Heterogeneous Copper Catalyst A schematic of the one embodiment of the centrifuge column comprising the heterogeneous copper catalyst is shown in FIG. 2. The apparatus consists of a modified Bio Rad microspin column (2 cm diameter) preloaded with ~100 µL of 1 to 6 kDa size-exclusion resin (Bio-Gel P-6 media). Small pellets (~1 mm diameter) of amalgamated zinc were mixed into 400 µL of an ion-exchange slurry in either ammonium acetate buffer (0.1 M, pH 7.5) or 0.1% aqueous trifluoroacetic acid, then layered on top of the column. Next, 500 µL of a 10 mM solution of either $Cu^{II}(phendione)_2^{2+}$ (for cation-exchange resins, Sephadex-CM C-50; phendione is 1,10-phenanthroline-5,6-dione) or $Cu^{II}(bathophen)_2^{2-}$ (for anion-exchange resins, Sephadex-DEAE A-50; bathophen is 4,7-diphenyl-1-1,10-phenanthroline-disulfonic acid disodium salt) were added to the top of the column and immobilized onto the matrix by spinning at 1000 rpm for 1 minute in a microcentrifuge. The column was washed several times with deoxygenated buffer, after which the ion-exchange layer appeared as an intense olive green color, indicating the presence of catalytically active $Cu^{I}(phendione)_2^+$ or $Cu^{I}(bathophen)_2^-$. Columns prepared in this fashion are optionally stored in the refrigerator for at least two months prior to use, with no deterioration in their activity.

Example 3

Preparation of Glycosylated DNA

Matrix Preparation

Approximately 250 µL of CM-52 cation-exchange resin was suspended in an equal volume of 50 mM ammonium acetate buffer pH 6.5. A separate 150 µL aliquot of CM-52 was similarly suspended in an aqueous solution (10 mM) of $Cu(phendione)_2^{2+}$ that had been previously degassed with argon. Before preparing the column, a small amount of zinc amalgam (4 or 5 grains) was added to the CM-52/Cu$(phendione)_2^{2+}$ mixture and shaken until it turned dark green.

Centrifuge Column Preparation

The centrifuge column consisted of a modified Bio Rad Micro spin Chromatography column. The commercial column was opened and the majority of the pre-packed size-exclusion gel (P-6 polyacrylamide gel, size exclusion limit 1 to 6 kDa) was extracted, leaving only a small amount (~100 µL) suspended in tris buffer. A small amount (~200 µL) of the pure ion-exchange resin was layered on top, followed by another ~200 µL of the ion-exchange resin containing Cu (I) and zinc amalgam. The resulting column was washed 5 times with 100 µl of degassed 50 mM ammonium acetate buffer by spinning the column for 2 minutes at 1000×g in a microcentrifuge.

Heterogeneous Copper-Catalyzed Azide-Alkyne Cycloaddition

50 µl of 200 µM ethynyl-labeled DNA (5'-ethynyl-$(CH_2)_6$–GCTCAGTACGACGTCGA-3' (SEQ ID NO: 2); MW 5355.5 g/mol; 200 µM) was combined with 50 µof 1-azido-1-deoxy-β-D-galactopyranoside ranging in concentration from 200 µM to 20 mM. This solution was added to a spin column prepared using the cation exchange resin as described above and spun for 3 minutes at 1000×g. The column was then washed with five 100 µl aliquots of 50 mM ammonium acetate buffer, each time spinning for 2 min at 1000×g. The washes were collected and combined with the initial reaction.

HPLC analysis was used to determine the purity of the glycosylated DNA prepared. For comparison, the same DNA glycosylation reaction was performed via a more conventional approach, using $Cu(phendione)_2^{2+}$ (1 mM) with sodium ascorbate (10 mM). HPLC analysis was carried out using an Agilent Model 1100 HPLC equipped with a Varian Dynamax 250×10 mm C18 column. DNA samples were eluted with a mixture of acetonitrile and 50 mM ammonium acetate buffer. The initial gradient was 3% acetonitrile for 5 minutes, ramped to a final concentration of 35% over 60 minutes.

Figure 3A:
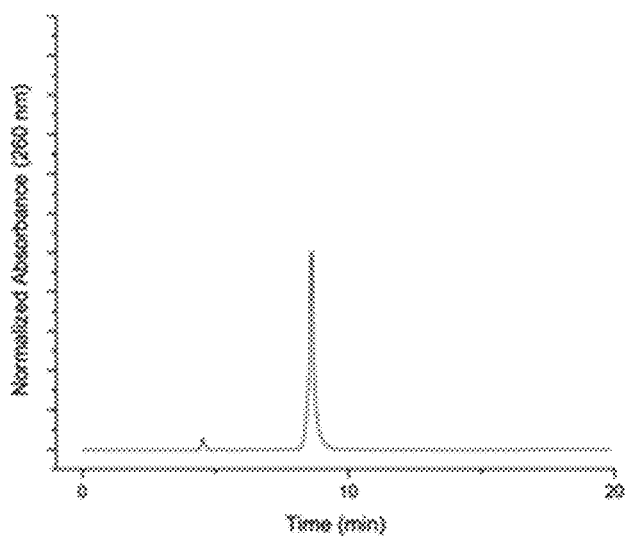
FIG. 3A and FIG. 3B depict the HPLC traces for crude product following DNA-ethynyl/azido-glucose conjugation via centrifuge column, or spin column, (FIG. 3A) and conventional solution-phase coupling using sodium ascorbate as the reducing agent (FIG. 3B).
Figure 3B:
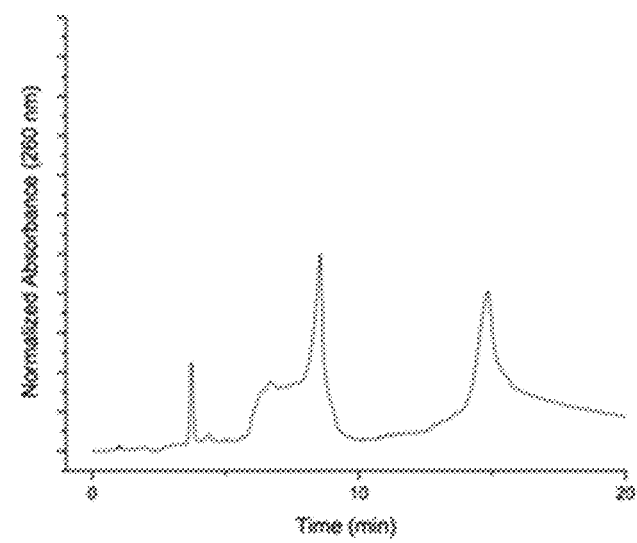

The HPLC chromatogram for the centrifuge column, or spin column, reaction yielded the remarkably clean trace shown in FIG. 3A, indicating the presence of only the desired product in the solution. The yield was determined by drying down the product collected from the HPLC, followed by re-suspending it in a known quantity of buffer. The yield of the glycosylated DNA was typically isolated in >85% yield. The near-quantitative yield and essentially pure product obtained via the centrifuge column is in sharp contrast to the more conventional solution-phase reaction. FIG. 3B depicts the resulting HPLC chromatogram of the product from the conventional approach and the chromatogram clearly shows several species in the mixture, indicating that further purification is necessary to isolate the product.

Products were confirmed by MALDI-MS analysis. 3-hydroxypicolinic acid (3-HPA) was used for the MALDI matrix, consisting of 70 mg 3-HPA with 7 mg diammonium citrate in 1.5 mL 10:1 deionized water:acetonitrile. The crude glycosylated DNA products were dried under vacuum, desalted, and then spotted onto the MALDI sample plate with an equi-volume amount of the prepared 3-HPA matrix.

Example 4

Preparation of Fluorescent Peptide

Matrix Preparation

The anionic resin was prepared in a similar fashion as described for the Matrix Preparation Section of Example 3. In this preparation, DE-52 anion-exchange resin was suspended in 0.1% trifluoroacetic acid (TFA) in deionized water and 10 mM aqueous $Cu(bathophenanthroline)_2^{2-}$ was used as the copper (II) precatalyst.

Centrifuge Column Preparation

The centrifuge column consisted of a modified Bio Rad Micro spin Chromatography column. The commercial column was opened and the majority of the pre-packed size-exclusion gel (P-6 polyacrylamide gel, size exclusion limit 1 to 6 kDa) was extracted, leaving only a small amount (~100 μL) suspended in tris buffer. A small amount (~200 μL) of the pure ion-exchange resin was layered on top, followed by another ~200 μL of the ion-exchange resin containing Cu (I) and zinc amalgam. The resulting column was washed 5 times with 100 μl of degassed 50 mM ammonium acetate buffer by spinning the column for 2 minutes at 1000×g in a microcentrifuge.

Heterogeneous Copper-Catalyzed Azide-Alkyne Cycloaddition

The centrifuge column was washed with 300 μl of degassed 1% TFA in deionized water. Next, 50 μl of 8 mM coumarin-$N_3$ (fluorogenic dye 3-azido-7-hydroxycoumarin) in a 3:1 mixture of water:DMSO was combined with 50 μl of 8 mM 8-Arg (octa-arginine) (SEQ ID NO: 1) and bubble degassed with argon. The 8-Arg (SEQ ID NO: 1)/coumarin-$N_3$ mixture was loaded into the column and spun for 2 minutes at 1000×g. The column was then washed with five 100 μl aliquots of 1% TFA in distilled water. The washes were collected and combined with the initial reaction.

HPLC analysis was used to determine the purity of the coumarin-labeled 8-Arg (SEQ ID NO: 1). For comparison, we also carried out the same cycloaddition reaction with conventional solution-phase conjugation using sodium ascorbate as the reductant. HPLC analysis was carried out using an Agilent Model 1100 HPLC equipped with a Varian Dynamax 250×10 mm C18 column. 8-Arg (SEQ ID NO: 1) samples were eluted using 0.1% TFA in acetonitrile as the mobile phase and 0.1% TFA in deionized water as the aqueous phase. Initial conditions were 25% acetonitrile for 5 minutes ramped to 50% over 40 minutes.

Figure 4A:
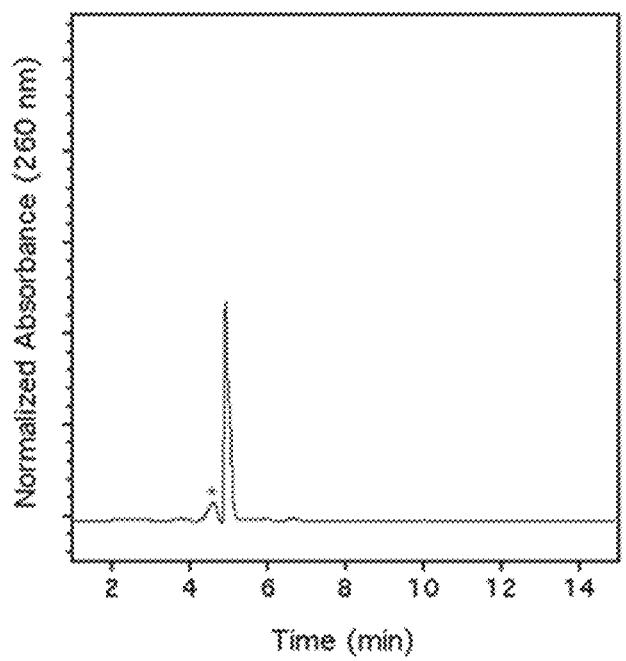
FIG. 4A and FIG. 4B depict the HPLC traces for crude product following 8-Arg/coumarin conjugation ("8-Arg" disclosed as SEQ ID NO: 1) via centrifuge column, or spin column, (FIG. 4A), and conventional solution-phase coupling using sodium ascorbate as the reducing agent (FIG. 4B). (*indicates 8-Arg (SEQ ID NO: 1) unmodified with an ethynyl group)
Figure 4B:
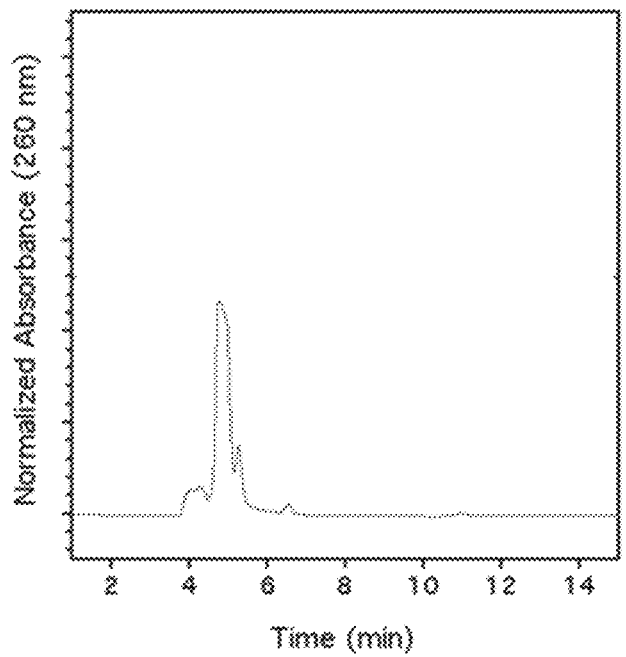

FIG. 4A and FIG. 4B show the HPLC traces of the crude products obtained from the centrifuge column (FIG. 4A) as well as the products obtained via conventional solution-phase conjugation using sodium ascorbate as the reductant (FIG. 4B). As observed with the glycosylated DNA reaction from Example 3, the centrifuge column, or spin-column, method results in essentially quantitative yield of coumarin-labeled 8-Arg (SEQ ID NO: 1).

Products were confirmed by MALDI-MS analysis. 3-hydroxypicolinic acid (3-HPA) was used for the MALDI matrix, consisting of 70 mg 3-HPA with 7 mg diammonium citrate in 1.5 mL 10:1 deionized water: acetonitrile. The crude coumarin-labeled 8-Arg (SEQ ID NO: 1) products were dried under vacuum, desalted, and then spotted onto the MALDI sample plate with an equi-volume amount of the prepared 3-HPA matrix.

Example 5

ICP-AES Analysis of Centrifuge Columns Containing Heterogeneous Copper Catalyst Matrix The columns described herein are used for these studies consisted of a modified Micro Bio-Spin column preloaded with ~100 μL Bio-Gel P-6 size exclusion media (1 to 6 kDa, See FIG. 2 as an example). Small pellets (~1 mm diameter) of amalgamated zinc were mixed into 400 μL of an ion-exchange slurry in either ammonium acetate buffer (0.1 M, pH 7.5) or 0.1% aqueous TFA, then layered on top of the column. Next, 500 μL of a 10 mM solution of either $Cu^{II}$(phendinone)$_2^{2+}$(for cation-exchange resins, Macro-Prep CM resin) or $Cu^{II}$(bathophen)$_2^{2-}$for anion-exchange resins, Macro-Prep DEAE resin) were added to the top of the column and immobilized onto the matrix by spinning at 1000×g for 1 min in a microcentrifuge. The column was washed several times with deoxygenated buffer, after which the ion-exchange layer appeared as an intense olive green color, indicated the presence of a catalytically active $Cu^I$ (phendione)$_2^+$or $Cu^I$(bathophen)$_2^{3-}$. The columns prepared in this fashion have been stored in the refrigerator for at least 2 months prior to use with no deterioration in their activity.

ICP-AES analysis was conducted with a Perkin Elmer Optima 7000 DV. A copper stock solution was prepared by dissolving copper(II) sulfate hexahydrate in double-distilled water and preparing appropriate dilutions with volumetric flasks to generate 0, 0.01, 0.05, and 0.2 mg/L standards. Eluent samples from the column were analyzed without additional preparation. For each standard and sample, the instrument was configured to average the intensity readings from two measurements.

Figure 5:
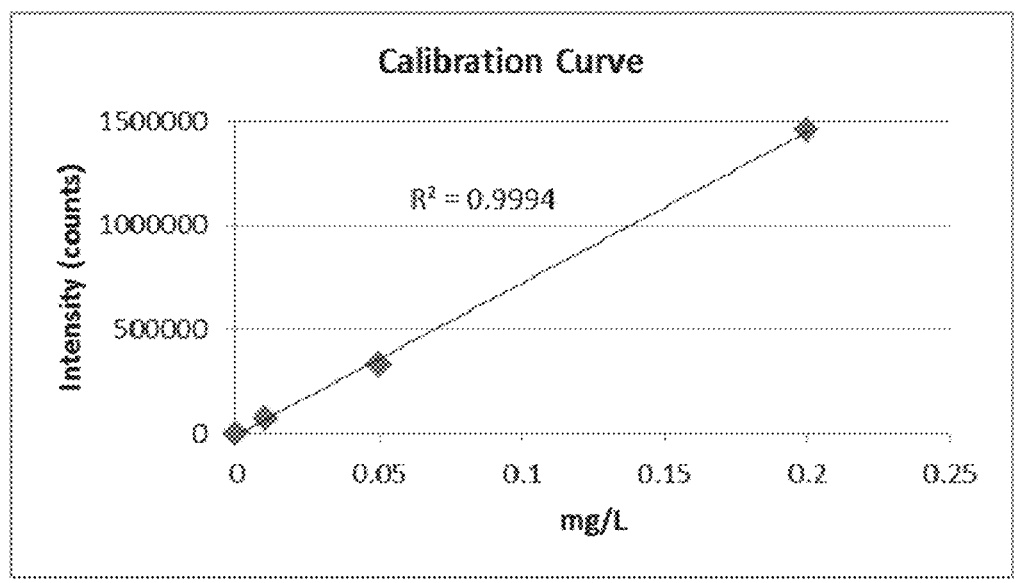
FIG. 5 depicts the calibration curve obtained for the ICP-AES analysis of Cu in spin column flow-through loaded with Cu-ligand catalyst.

FIG. 5 depicts the calibration curve obtained from the ICP-AES analysis of Cu in spin column flow-through loaded with Cu-ligand catalyst. Table 1 corresponds to the data obtained used to prepare the calibration curve depicted in FIG. 5.

TABLE 1

| mg/L | Mean Corrected Intensity | Std. Dev. |
|---|---|---|
| 0 | 1374.7 | 0.52 |
| 0.01 | 68877.7 | 61.05 |
| 0.05 | 329245.9 | 1411.51 |
| 0.2 | 1457178.3 | 26164.55 |

Table 2 depicts the amount of copper detected with each eluent sample analyzed (BP=. Cu(bathophen) and PD=Cu (phendione)). The calibration data indicated that 0.01 ppm approached the lower detection limit of the instrument. All samples but one (PD with 1 mM EDTA in eluent) were below the detection limit of the instrument. These results show that the columns show good stability even in the presence of strongly chelating ions as the ICP-AES analysis showed that there were no detectable copper ions in the flow-through in elution solutions containing up to 1 mM EDTA.

TABLE 2

| Entry | Sample | mg/L Cu | [Cu] (μM) |
|---|---|---|---|
| 1 | BP water wash | 0.003 | 0.047209895 |
| 2 | BP 0.001 mM EDTA | 0.002 | 0.031473263 |
| 3 | BP 1 mM EDTA | 0.002 | 0.031473263 |
| 4 | PD water wash | 0.002 | 0.031473263 |
| 5 | PD 0.001 mM EDTA | 0.003 | 0.047209895 |
| 6 | PD 1 mM EDTA | 0.193 | 3.037169924 |

Example 6

General Preparation of Bioconjugated Cycloaddition Compounds from Centrifuge Columns Containing Heterogeneous Copper Catalyst Matrix Using any one of the columns described herein, such as those described in the Examples section, the copper-catalyzed azide-alkyne reaction is carried out by pipetting onto the column a mixture of the appropriate reaction partners, such as a alkyne-labeled biomolecule, in the appropriate concentration, such as from about 10 μm to about 10 mM, and an azide-labeled ligand in the appropriate concentration ratio, such as a ratio ranging from about stoichiometric to 100-fold excess. The column is then subjected to spinning via a microcentrifuge for an appropriate amount of time, such as several minutes. The column is then washed with an appropriate solution followed by spinning for an appropriate amount of time to elute the product, such as the bioconjugated product.

In some embodiments, the mixture of appropriate reaction partners contain cells and/or cell lysates. In some instances, when the mixture of the appropriate reaction partners is passed through the column, the majority of the cells and/or cell lysates remain at the top of the column and do not pass through the column. In some instances, the bioconjugated product obtained is free or substantially free of impurities derived from the cells and/or cell lysates. In some instances, the bioconjugated product obtained contains trace impurities derived from the cells and/or cell lysates and a second purification is required to remove the trace impurities.

In some instances, the columns are stored in the refrigerator for a period of time prior to use, such as for at least two months with no deterioration in activity. In some instances, these columns are re-used without any apparent loss in activity.

What is claimed is:

1. A method for preparing a cycloaddition compound from a reaction catalyzed by a heterogeneous copper catalyst, comprising
  (a) mixing an alkyne component and an azide component in an appropriate solvent to form a solution;
  (b) transferring the solution containing the alkyne component and the azide component to a column with a matrix barrier at the bottom of the column;
  wherein the column comprises a matrix of a copper (II) precatalyst and a reducing agent; wherein a copper (I) catalyst is generated from the reduction of the copper (II) precatalyst with the reducing agent; and
  (c) passing the solution containing the alkyne component and the azide component through the column; wherein upon contact with the copper (I) catalyst within the matrix, the alkyne component and the azide component react to form the cycloaddition compound;
  wherein the column is suitable for use in centrifugal column chromatography; and
  wherein the column further comprises a 1 to 6 kDa size-exclusion resin.

2. The method of claim 1, wherein the alkyne component comprises a small molecule, a protein, a peptide, an amino acid, an oligonucleotide, a nucleotide, a nucleoside, a carbohydrate, or a fluorophore.

3. The method of claim 1, wherein the azide component comprises a small molecule, a protein, a peptide, an amino acid, an oligonucleotide, a nucleotide, a nucleoside, a carbohydrate, or a fluorophore.

4. The method of claim 1, wherein the alkyne component and/or the azide component contains cells and/or cell lysates.

5. The method of claim 1, wherein the copper (II) precatalyst further comprises a ligand.

6. The method of claim 1, wherein the reducing agent is zinc amalgam.

7. The method of claim 1, wherein the cycloaddition compound is a derivatized product from cell lysates.

8. The method of claim 7, wherein the derivatized product from cell lysates is free or substantially free of impurities derived from cell lysates.

9. A column matrix suitable for use in centrifugal column chromatography comprising a heterogeneous copper catalyst that catalyzes the azide-alkyne cycloaddition; wherein the column matrix further comprises a 1 to 6 kDa size-exclusion resin.

10. The column matrix of claim 9, wherein the heterogeneous copper catalyst comprises a copper (II) precatalyst and a reducing agent.

11. The column matrix of claim 10, wherein the reducing agent is zinc amalgam.

12. The column matrix of claim 9, wherein the column matrix further comprises an ion-exchange resin.

13. A column suitable for use in centrifugal column chromatography comprising a matrix of a heterogeneous copper catalyst that catalyzes the azidealkyne cycloaddition; wherein the column further comprises a 1to 6kDa size-exclusion resin.

14. The column of claim 13, wherein the heterogeneous copper catalyst comprises a copper (II) precatalyst and a reducing agent.

15. The column of claim 14, wherein the reducing agent is zinc amalgam.

16. The column of claim 13, wherein the matrix further comprises an ion-exchange resin.

17. The column matrix of claim 10, wherein the copper (II) precatalyst further comprises a ligand.

18. The column of claim 14, wherein the copper (II) precatalyst further comprises a ligand.

19. The method of claim 1, wherein the size-exclusion resin comprises a resin that is polystyrene-based, polysaccharide-based, polyamide-based, carbon-based, alumina-based, or silica-based, or any combination thereof.

20. The method of claim 1, wherein the column further comprises an ion-exchange resin that is polystyrene-based, polysaccharide-based, polyethylenimine-based, or polyamide-based.

21. The column matrix of claim 9, wherein the size-exclusion resin comprises a resin that is polystyrene-based, polysaccharide-based, polyamide-based, carbon-based, alumina-based, or silica-based, or any combination thereof.

22. The column matrix of claim 12, wherein the ion-exchange resin is polystyrene-based, polysaccharide-based, poiyethyienirnine-based, or polyamide-based.

23. The column of claim 13, wherein the size-exclusion resin comprises a resin that is polystyrene-based, polysaccharide-based, polyamide-based, carbon-based, alumina-based, or silica-based, or any combination thereof.

24. The column of claim 16, wherein the ion-exchange resin is polystyrene-based, polysaccharide-based, polyethylenimine-based, or polyamide-based.

* * * * *

UNITED STATES PATENT AND TRADEMARK OFFICE
CERTIFICATE OF CORRECTION

PATENT NO. : 9,879,044 B2  
APPLICATION NO. : 15/168911  
DATED : January 30, 2018  
INVENTOR(S) : Michael Hill and Andrew Udit Page 1 of 1

It is certified that error appears in the above-identified patent and that said Letters Patent is hereby corrected as shown below:

In the Claims

Column 46, Line 6:
In Claim 1, the portion "the column matrix further comprises a 1to 6kDa" should read --the column matrix further comprises a 1 to 6 kDa--

Column 46, Line 61:
In Claim 9, the portion "the column matrix further comprises a 1to 6kDa" should read --the column matrix further comprises a 1 to 6 kDa--

Column 47, Line 6:
In Claim 13, the portion "the column matrix further comprises a 1to 6kDa" should read --the column matrix further comprises a 1 to 6 kDa--

Signed and Sealed this  
Tenth Day of July, 2018

Andrei Iancu  
*Director of the United States Patent and Trademark Office*